(12) United States Patent
Lupton

(10) Patent No.: US 6,555,370 B1
(45) Date of Patent: Apr. 29, 2003

(54) BIFUNCTIONAL SELECTABLE FUSION GENES

(75) Inventor: Stephen D. Lupton, Seatle, WA (US)

(73) Assignee: Immunex Corporation, Seattle, WA (US)

(*) Notice: Subject to any disclaimer, the term of this patent is extended or adjusted under 35 U.S.C. 154(b) by 0 days.

(21) Appl. No.: 08/483,941

(22) Filed: Jun. 7, 1995

Related U.S. Application Data

(63) Continuation of application No. 08/066,388, filed on May 21, 1993, now abandoned, which is a continuation-in-part of application No. 07/791,932, filed on Nov. 12, 1991, now abandoned, which is a continuation-in-part of application No. 07/612,326, filed on Nov. 13, 1990, now abandoned.

(51) Int. Cl.[7] .................... C12N 15/62; C12N 15/10; C12N 5/10

(52) U.S. Cl. ............... 435/325; 536/23.2; 536/23.4; 435/69.7; 435/70.3; 435/440; 435/455; 435/456; 435/252.3; 435/320.1

(58) Field of Search ................ 536/23.2, 23.4; 435/69.7, 70.3, 172.1, 172.3, 240.2, 252.3, 320.1, 325, 440, 455, 456; 935/10, 32, 34, 47, 57, 70, 79

(56) References Cited

U.S. PATENT DOCUMENTS

| | | | | |
|---|---|---|---|---|
| 4,960,704 A | * | 10/1990 | Ingolia et al. | 435/252.33 |
| 5,166,059 A | * | 11/1992 | Pastan et al. | 435/69.7 |
| 5,317,096 A | * | 5/1994 | De Greve et al. | 536/23.71 |
| 5,358,866 A | * | 10/1994 | Mullen et al. | 435/240.2 |

FOREIGN PATENT DOCUMENTS

| | | | |
|---|---|---|---|
| EP | 0293193 | | 11/1988 |
| EP | 0402108 | | 12/1990 |
| EP | 0415731 | | 3/1991 |
| WO | WO 92/08796 | | 5/1992 |
| WO | 9301281 | * | 1/1993 |
| WO | WO 93/21959 | | 11/1993 |

OTHER PUBLICATIONS

F. Schwartz et al., "A dominant positive and negative selectable gene for use in mammalian cells", Proc. Natl. Acad. Sci. 88: 10416–10420, Dec. 1991.*

S.D. Lupton et al., "Dominant Positive and Negative Selection Using a Hygromycin Phosphotransferase–Thymidine Kinase Fusion Gene", Mol. Cell. Biol. 11(6): 3374–3378, Jun. 1991.*

Austin, E.A., et al., "A first step in the development of gene therapy for colorectal carcinoma: cloning, sequencing, and expression of *Escherichia coli* cytosine deaminase" *Mol. Pharmacol.* (1993) 43(3):380–387.

Danielsen, S., et al., "Characterization of the *Escherichia coli* codBA operon encoding cytosine permease and cytosine deaminase" *Mol. Microbiol.* (1992) 6(10):1335–1344.

Reiss, et al., "Protein fusions with the kanamycin resistance gene from transposon Tn5" *EMBO J.* (1984) 3:3317–3322.

Peabody et al., "Termination–reinitiation occurs in the translation of mammalian cell mRNAs" *Mol. Cell. Biol.* (1986) 6:2695–2703.

Schwartz, et al., "A dominant positive and negative selectable gene for use in mammalian cells" *Proc. Natl. Acad. Sci. USA* (1991) 88:10416–10420.

Reynes, et al., "A thmidine kinase and zeocin resistance encoding new hybrid gene for positive and negative selection in mammalian cells", in Abstracts of papers presented at the 1994 meeting on Gene Therapy, Sep. 21–25, 1994, Cold Spring Harbor (1994).

U.S. patent application Ser. No. 07/365,567, filed Jun. 14, 1989.

U.S. patent application Ser. No. 07/062,583, filed Jun. 16, 1987.

U.S. patent application Ser. No. 07/202,783, filed Jun. 3, 1988.

Borrelli et al., "Targeting of an inducible toxic phenotype in animal cells" *Proc. Natl. Acad. Sci. USA* (1988) 85:7572–7576.

McKnight, "The nucleotide sequence and transcript map of the herpes simplex virus thymidine kinase gene" *Nucleic Acids Res.* (1980) 8(24):5949–5964.

Sugden et al., "A vector that replicates as a plasmid and can be efficiently selected in b–lymphocytes transformed by Epstein–Barr virus" *Mol. Cell. Biol.* (1985) 5:410–413.

Kaster et al., "Analysis of a bacterial hygromycin B resistance gene by transcriptional and translational fusions and by DNA sequencing" *Nucleic Acids Res.* (1983) 11:6895–6911.

Shapira et al., "Hybrid protein thymidine kinase gene fusions: plasmid vectors for the study of transcription and translation initiation signals" (1987) *Gene* 52:8394.

(List continued on next page.)

Primary Examiner—Rebecca E. Prouty
(74) Attorney, Agent, or Firm—Morrison & Foerster LLP

(57) ABSTRACT

The invention provides selectable fusion genes including a dominant positive selectable gene fused to and in reading frame with a negative selectable gene. The selectable fusion gene encodes a single bifunctional fusion protein which is capable of conferring a dominant positive selectable phenotype and a negative selectable phenotype on a cellular host. A dominant positive selectable phenotype is conferred, for example, by the hph gene for hygromycin B resistance (Hm$^r$). A dominant negative selectable phenotype is conferred, for example, by the HSV-I TK gene for ganciclovir sensitivity (GCV$^s$). A dominant positive selectable phenotype is also conferred by the neo gene for G-418 aminoglycoside antibiotic resistance (G-418$^r$). A dominant negative selectable phenotype is also conferred by the CD gene for 5-fluorocytosine sensitivity (5-FC$^s$). The present invention also provides recombinant expression vectors, such as retroviral vectors, which include selectable fusion genes, and cells transduced with the recombinant expression vectors. The bifunctional selectable fusion genes are expressed and regulated as a single genetic entity, permitting co-regulation and co-expression with a high degree of efficiency.

10 Claims, 12 Drawing Sheets

OTHER PUBLICATIONS

MacNeil et al., "Yeast/herpes simplex virus thymidine kinase gene fusions yield fusion proteins with thymidine kinase activity" *Current Genetics* (1985) 9:567–572.

Reiss et al., "Protein fusions with the kanamycin resistance gene from transposon Tn5" *Embo J.* (1984) 3:3317–3322.

Overell et al., "Stably transmitted triple–promoter retroviral vectors and their use in transformation of primary mammalian cells" *Mol. Cell. Biol.* (1988) 8:1803–1808.

Reid et al., "Regulatory elements in the introns of the human HPRT gene are necessary for its expression in embryonic stem cells" *Proc. Natl. Acad. Sci. USA* (1990) 87:4299–4303.

Wigler et al., "Transformation of mammalian cells with genes from procaryotes and eucaryotes" *Cell 16* (1979) pp. 777–785.

Emerman et al., "Quantitative analysis of gene suppression in integrated retrovirus vectors" *Mol. Cell. Biol.* (1986) 6:792–800.

Kaufman et al., "Translational efficiency of polycistronic mRNAs and their utilization to express heterologous genes in mammalian cells" *EMBO J* (1988) 6:187–193.

Heyman et al., "Thymidine kinase obliteration: creation of transgenic mice with controlled immune deficiency" *Proc Natl Acad Sci USA* (1989) 86:2698–2702.

Moolten et al., "Lymphoma regression induced by ganciclovir in mice bearing a herpes thymidine kinase transgene" *Human Gene Therapy 1* (1990) pp. 125–134.

Moolten et al., "Curability of tumors bearing herpes thymidine kinase genes transferred by retroviral vectors" *J. Natl. Cancer Inst.* (1990) 82:297–300.

Mann et al., "Construction of a retrovirus packaging mutant and its use to produce helper–free defective retrovirus" *Cell* (1983) 33:153–159.

Miller et al., "Redesign of retrovirus packaging cell lines to avoid recombination leading to helper virus production" *Mol. Cell. Biol.* (1986) 6:2895–2902.

Miller, "Retrovirus packaging cells" *Human Gene Therapy* (1990) 1:5–14.

Williams et al., "Introduction of new genetic material into pluripotent haematopoietic stem cells of the mouse" *Nature* (1984) 310:476–480.

Dick et al., "Introduction of a selectable gene into primitive stem cells capable of long–term reconstitution of the hempoietic system of W/W$^v$ mice" *Cell* (1985) 42:71–79.

Keller et al., "Expression of a foreign gene in myeloid and lymphoid cells derived from multipotent haematopoietic precursors" *Nature* (1985) 318:149–154.

Rosenberg et al., "Gene transfer into humans—immunotherapy of patients with advanced melanoma, using tumor-infiltrating lymphocytes modified by retroviral gene transduction" *New Engl. J. Med.* (1990) 323:570–578.

Kasid et al., "Human gene transfer: characterization of human tumor–infiltrating lymphocytes as vehicles for retroviral–mediated gene transfer in man" *Proc. Natl. Acad. Sci. USA* (1990) 87:473–477.

Germann et al., "Retroviral transfer of a chimeric multidrug resistance–adenosine deaminase gene" *J. Biol. Chem.* (1989) 264:7418–7424.

Colpére–Garapin et al., "A new dominant selective marker for higher eukaryotic cells" *J. Mol. Biol.* (1981) 150:1–14.

Lassare et al., "Differential expression of two linked selection genes (HSVItk and Eco–gpt) in transformed terato–carcinoma and in L cells" *J. Cell. Physiol.* (1985) 124:37–42.

Beck et al., "Nucleotide sequence and exact localization of the neomycin phosphotransferase gene from transposon Tn5" *Gene* (1982) 19:327.

Lupton et al., "Dominant positive and negative selection using a hygromycin phosphotransferase–thymidine kinase fusion gene" *Mol. Cell. Biol.* (1991) 11(6):3374–3378.

Mullen et al., "Transfer of the bacterial gene for cytosine deaminase to mammalian cells confers lethal sensitivity to 5–fluorocytosine: a negative selection system" *Proc. Natl. Acad. Sci. USA* (1992) 89:33.

Oldfield et al., "Gene therapy for the treatment of brain tumors using intra–tumoral transduction with the thymidine kinase gene and intravenous ganciclovir" *Human Gene Therapy* (1993) 4:39.

Oldfield et al., "Gene therapy for the treatment of brain tumors using intra–tumoral transduction with the thymidine kinase gene and intravenous ganciclovir 92–N–0246" *Human Gene Therapy* (1993) 4:60–69.

* cited by examiner

CMV = Cytomegalovirus
hygro = hygromycin transferase gene
neo = bacterial neomycin phosphotransferase
CD = cytosine deaminase gene
LTR = Long Terminal Repeat
A+ = polyadenylation signal tgLS (+) neo tgLS (+) CD-neo LTR = Long Terminal Repeat neo = bacterial neomycin phosphotransferase CD = cytosine deaminase gene A+ = polyadenylation signal

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 2076 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..2073

(xi) SEQUENCE DESCRIPTION: SEQ ID NO:1:

```
ATG AAA AAG CCT GAA CTC ACC GCG ACG TCT GTC GAG AAG TTT CTG ATC        48
Met Lys Lys Pro Glu Leu Thr Ala Thr Ser Val Glu Lys Phe Leu Ile
 1               5                  10                  15

GAA AAG TTC GAC AGC GTC TCC GAC CTG ATG CAG CTC TCG GAG GGC GAA        96
Glu Lys Phe Asp Ser Val Ser Asp Leu Met Gln Leu Ser Glu Gly Glu
                20                  25                  30

GAA TCT CGT GCT TTC AGC TTC GAT GTA GGA GGG CGT GGA TAT GTC CTG       144
Glu Ser Arg Ala Phe Ser Phe Asp Val Gly Gly Arg Gly Tyr Val Leu
            35                  40                  45

CGG GTA AAT AGC TGC GCC GAT GGT TTC TAC AAA GAT CGT TAT GTT TAT       192
Arg Val Asn Ser Cys Ala Asp Gly Phe Tyr Lys Asp Arg Tyr Val Tyr
        50                  55                  60

CGG CAC TTT GCA TCG GCC GCG CTC CCG ATT CCG GAA GTG CTT GAC ATT       240
Arg His Phe Ala Ser Ala Ala Leu Pro Ile Pro Glu Val Leu Asp Ile
    65                  70                  75                  80

GGG GAA TTC AGC GAG AGC CTG ACC TAT TGC ATC TCC CGC CGT GCA CAG       288
Gly Glu Phe Ser Glu Ser Leu Thr Tyr Cys Ile Ser Arg Arg Ala Gln
```

```
                    85                    90                     95
GGT GTC ACG TTG CAA GAC CTG CCT GAA ACC GAA CTG CCC GCT GTT CTG        336
Gly Val Thr Leu Gln Asp Leu Pro Glu Thr Glu Leu Pro Ala Val Leu
            100                 105                 110

CAG CCG GTC GCG GAG GCC ATG GAT GCG ATC GCT GCG GCC GAT CTT AGC        384
Gln Pro Val Ala Glu Ala Met Asp Ala Ile Ala Ala Ala Asp Leu Ser
            115                 120                 125

CAG ACG AGC GGG TTC GGC CCA TTC GGA CCG CAA GGA ATC GGT CAA TAC        432
Gln Thr Ser Gly Phe Gly Pro Phe Gly Pro Gln Gly Ile Gly Gln Tyr
        130                 135                 140

ACT ACA TGG CGT GAT TTC ATA TGC GCG ATT GCT GAT CCC CAT GTG TAT        480
Thr Thr Trp Arg Asp Phe Ile Cys Ala Ile Ala Asp Pro His Val Tyr
145                 150                 155                 160

CAC TGG CAA ACT GTG ATG GAC GAC ACC GTC AGT GCG TCC GTC GCG CAG        528
His Trp Gln Thr Val Met Asp Asp Thr Val Ser Ala Ser Val Ala Gln
                165                 170                 175

GCT CTC GAT GAG CTG ATG CTT TGG GCC GAG GAC TGC CCC GAA GTC CGG        576
Ala Leu Asp Glu Leu Met Leu Trp Ala Glu Asp Cys Pro Glu Val Arg
            180                 185                 190

CAC CTC GTG CAC GCG GAT TTC GGC TCC AAC AAT GTC CTG ACG GAC AAT        624
His Leu Val His Ala Asp Phe Gly Ser Asn Asn Val Leu Thr Asp Asn
            195                 200                 205

GGC CGC ATA ACA GCG GTC ATT GAC TGG AGC GAG GCG ATG TTC GGG GAT        672
Gly Arg Ile Thr Ala Val Ile Asp Trp Ser Glu Ala Met Phe Gly Asp
        210                 215                 220

TCC CAA TAC GAG GTC GCC AAC ATC TTC TTC TGG AGG CCG TGG TTG GCT        720
Ser Gln Tyr Glu Val Ala Asn Ile Phe Phe Trp Arg Pro Trp Leu Ala
225                 230                 235                 240

TGT ATG GAG CAG CAG ACG CGC TAC TTC GAG CGG AGG CAT CCG GAG CTT        768
Cys Met Glu Gln Gln Thr Arg Tyr Phe Glu Arg Arg His Pro Glu Leu
                245                 250                 255

GCA GGA TCG CCG CGG CTC CGG GCG TAT ATG CTC CGC ATT GGT CTT GAC        816
Ala Gly Ser Pro Arg Leu Arg Ala Tyr Met Leu Arg Ile Gly Leu Asp
            260                 265                 270

CAA CTC TAT CAG AGC TTG GTT GAC GGC AAT TTC GAT GAT GCA GCT TGG        864
Gln Leu Tyr Gln Ser Leu Val Asp Gly Asn Phe Asp Asp Ala Ala Trp
            275                 280                 285

GCG CAG GGT CGA TGC GAC GCA ATC GTC CGA TCC GGA GCC GGG ACT GTC        912
Ala Gln Gly Arg Cys Asp Ala Ile Val Arg Ser Gly Ala Gly Thr Val
        290                 295                 300

GGG CGT ACA CAA ATC GCC CGC AGA AGC GCG GCC GTC TGG ACC GAT GGC        960
Gly Arg Thr Gln Ile Ala Arg Arg Ser Ala Ala Val Trp Thr Asp Gly
305                 310                 315                 320

TGT GTA GAA GTC GCG TCT GCG TTC GAC CAG GCT GCG CGT TCT CGC GGC       1008
Cys Val Glu Val Ala Ser Ala Phe Asp Gln Ala Ala Arg Ser Arg Gly
                325                 330                 335

CAT AGC AAC CGA CGT ACG GCG TTG CGC CCT CGC CGG CAG CAA GAA GCC       1056
His Ser Asn Arg Arg Thr Ala Leu Arg Pro Arg Arg Gln Gln Glu Ala
            340                 345                 350

ACG GAA GTC CGC CCG GAG CAG AAA ATG CCC ACG CTA CTG CGG GTT TAT       1104
Thr Glu Val Arg Pro Glu Gln Lys Met Pro Thr Leu Leu Arg Val Tyr
            355                 360                 365

ATA GAC GGT CCC CAC GGG ATG GGG AAA ACC ACC ACC ACG CAA CTG CTG       1152
Ile Asp Gly Pro His Gly Met Gly Lys Thr Thr Thr Thr Gln Leu Leu
        370                 375                 380

GTG GCC CTG GGT TCG CGC GAC GAT ATC GTC TAC GTA CCC GAG CCG ATG       1200
Val Ala Leu Gly Ser Arg Asp Asp Ile Val Tyr Val Pro Glu Pro Met
385                 390                 395                 400

ACT TAC TGG CGG GTG CTG GGG GCT TCC GAG ACA ATC GCG AAC ATC TAC       1248
```

```
Thr Tyr Trp Arg Val Leu Gly Ala Ser Glu Thr Ile Ala Asn Ile Tyr
            405                 410                 415

ACC ACA CAA CAC CGC CTC GAC CAG GGT GAG ATA TCG GCC GGG GAC GCG      1296
Thr Thr Gln His Arg Leu Asp Gln Gly Glu Ile Ser Ala Gly Asp Ala
            420                 425                 430

GCG GTG GTA ATG ACA AGC GCC CAG ATA ACA ATG GGC ATG CCT TAT GCC      1344
Ala Val Val Met Thr Ser Ala Gln Ile Thr Met Gly Met Pro Tyr Ala
            435                 440                 445

GTG ACC GAC GCC GTT CTG GCT CCT CAT ATC GGG GGG GAG GCT GGG AGC      1392
Val Thr Asp Ala Val Leu Ala Pro His Ile Gly Gly Glu Ala Gly Ser
450                 455                 460

TCA CAT GCC CCG CCC CCG GCC CTC ACC CTC ATC TTC GAC CGC CAT CCC      1440
Ser His Ala Pro Pro Pro Ala Leu Thr Leu Ile Phe Asp Arg His Pro
465                 470                 475                 480

ATC GCC GCC CTC CTG TGC TAC CCG GCC GCG CGG TAC CTT ATG GGC AGC      1488
Ile Ala Ala Leu Leu Cys Tyr Pro Ala Ala Arg Tyr Leu Met Gly Ser
            485                 490                 495

ATG ACC CCC CAG GCC GTG CTG GCG TTC GTG GCC CTC ATC CCG CCG ACC      1536
Met Thr Pro Gln Ala Val Leu Ala Phe Val Ala Leu Ile Pro Pro Thr
            500                 505                 510

TTG CCC GGC ACC AAC ATC GTG CTT GGG GCC CTT CCG GAG GAC AGA CAC      1584
Leu Pro Gly Thr Asn Ile Val Leu Gly Ala Leu Pro Glu Asp Arg His
            515                 520                 525

ATC GAC CGC CTG GCC AAA CGC CAG CGC CCC GGC GAG CGG CTG GAC CTG      1632
Ile Asp Arg Leu Ala Lys Arg Gln Arg Pro Gly Glu Arg Leu Asp Leu
530                 535                 540

GCT ATG CTG GCT GCG ATT CGC CGC GTT TAC GGG CTA CTT GCC AAT ACG      1680
Ala Met Leu Ala Ala Ile Arg Arg Val Tyr Gly Leu Leu Ala Asn Thr
545                 550                 555                 560

GTG CGG TAT CTG CAG TGC GGC GGG TCG TGG CGG GAG GAC TGG GGA CAG      1728
Val Arg Tyr Leu Gln Cys Gly Gly Ser Trp Arg Glu Asp Trp Gly Gln
            565                 570                 575

CTT TCG GGG ACG GCC GTG CCG CCC CAG GGT GCC GAG CCC CAG AGC AAC      1776
Leu Ser Gly Thr Ala Val Pro Pro Gln Gly Ala Glu Pro Gln Ser Asn
            580                 585                 590

GCG GGC CCA CGA CCC CAT ATC GGG GAC ACG TTA TTT ACC CTG TTT CGG      1824
Ala Gly Pro Arg Pro His Ile Gly Asp Thr Leu Phe Thr Leu Phe Arg
            595                 600                 605

GCC CCC GAG TTG CTG GCC CCC AAC GGC GAC CTG TAT AAC GTG TTT GCC      1872
Ala Pro Glu Leu Leu Ala Pro Asn Gly Asp Leu Tyr Asn Val Phe Ala
            610                 615                 620

TGG GCC TTG GAC GTC TTG GCC AAA CGC CTC CGT TCC ATG CAC GTC TTT      1920
Trp Ala Leu Asp Val Leu Ala Lys Arg Leu Arg Ser Met His Val Phe
625                 630                 635                 640

ATC CTG GAT TAC GAC CAA TCG CCC GCC GGC TGC CGG GAC GCC CTG CTG      1968
Ile Leu Asp Tyr Asp Gln Ser Pro Ala Gly Cys Arg Asp Ala Leu Leu
                    645                 650                 655

CAA CTT ACC TCC GGG ATG GTC CAG ACC CAC GTC ACC ACC CCC GGC TCC      2016
Gln Leu Thr Ser Gly Met Val Gln Thr His Val Thr Thr Pro Gly Ser
            660                 665                 670

ATA CCG ACG ATA TGC GAC CTG GCG CGC ACG TTT GCC CGG GAG ATG GGG      2064
Ile Pro Thr Ile Cys Asp Leu Ala Arg Thr Phe Ala Arg Glu Met Gly
            675                 680                 685

GAG GCT AAC TGA                                                      2076
Glu Ala Asn
    690
```

(2) INFORMATION FOR SEQ ID NO:2:

(i) SEQUENCE CHARACTERISTICS:

(A) LENGTH: 691 amino acids
(B) TYPE: amino acid
(D) TOPOLOGY: linear (ii) MOLECULE TYPE: protein (xi) SEQUENCE DESCRIPTION: SEQ ID NO:2:

```
Met Lys Lys Pro Glu Leu Thr Ala Thr Ser Val Glu Lys Phe Leu Ile
 1               5                  10                  15

Glu Lys Phe Asp Ser Val Ser Asp Leu Met Gln Leu Ser Glu Gly Glu
                20                  25                  30

Glu Ser Arg Ala Phe Ser Phe Asp Val Gly Gly Arg Gly Tyr Val Leu
            35                  40                  45

Arg Val Asn Ser Cys Ala Asp Gly Phe Tyr Lys Asp Arg Tyr Val Tyr
 50                  55                  60

Arg His Phe Ala Ser Ala Ala Leu Pro Ile Pro Glu Val Leu Asp Ile
 65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
            115                 120                 125

Gln Thr Ser Gly Phe Gly Pro Phe Gly Pro Gln Gly Ile Gly Gln Tyr
130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
            195                 200                 205

Gly Arg Ile Thr Ala Val Ile Asp Trp Ser Glu Ala Met Phe Gly Asp
210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
            275                 280                 285

Ala Gln Gly Arg Cys Asp Ala Ile Val Arg Ser Gly Ala Gly Thr Val
290                 295                 300

Gly Arg Thr Gln Ile Ala Arg Arg Ser Ala Ala Val Trp Thr Asp Gly
305                 310                 315                 320

Cys Val Glu Val Ala Ser Ala Phe Asp Gln Ala Ala Arg Ser Arg Gly
                325                 330                 335

His Ser Asn Arg Arg Thr Ala Leu Arg Pro Arg Gln Gln Glu Ala
            340                 345                 350

Thr Glu Val Arg Pro Glu Gln Lys Met Pro Thr Leu Leu Arg Val Tyr
            355                 360                 365

Ile Asp Gly Pro His Gly Met Gly Lys Thr Thr Thr Gln Leu Leu
370                 375                 380
```

```
Val Ala Leu Gly Ser Arg Asp Asp Ile Val Tyr Val Pro Glu Pro Met
385                 390                 395                 400

Thr Tyr Trp Arg Val Leu Gly Ala Ser Glu Thr Ile Ala Asn Ile Tyr
            405                 410                 415

Thr Thr Gln His Arg Leu Asp Gln Gly Glu Ile Ser Ala Gly Asp Ala
            420                 425                 430

Ala Val Val Met Thr Ser Ala Gln Ile Thr Met Gly Met Pro Tyr Ala
            435                 440                 445

Val Thr Asp Ala Val Leu Ala Pro His Ile Gly Glu Ala Gly Ser
    450                 455                 460

Ser His Ala Pro Pro Ala Leu Thr Leu Ile Phe Asp Arg His Pro
465             470                 475                 480

Ile Ala Ala Leu Leu Cys Tyr Pro Ala Ala Arg Tyr Leu Met Gly Ser
            485                 490                 495

Met Thr Pro Gln Ala Val Leu Ala Phe Val Ala Leu Ile Pro Pro Thr
            500                 505                 510

Leu Pro Gly Thr Asn Ile Val Leu Gly Ala Leu Pro Glu Asp Arg His
            515                 520                 525

Ile Asp Arg Leu Ala Lys Arg Gln Arg Pro Gly Glu Arg Leu Asp Leu
530                 535                 540

Ala Met Leu Ala Ala Ile Arg Arg Val Tyr Gly Leu Leu Ala Asn Thr
545                 550                 555                 560

Val Arg Tyr Leu Gln Cys Gly Gly Ser Trp Arg Glu Asp Trp Gly Gln
            565                 570                 575

Leu Ser Gly Thr Ala Val Pro Pro Gln Gly Ala Glu Pro Gln Ser Asn
            580                 585                 590

Ala Gly Pro Arg Pro His Ile Gly Asp Thr Leu Phe Thr Leu Phe Arg
            595                 600                 605

Ala Pro Glu Leu Leu Ala Pro Asn Gly Asp Leu Tyr Asn Val Phe Ala
            610                 615                 620

Trp Ala Leu Asp Val Leu Ala Lys Arg Leu Arg Ser Met His Val Phe
625                 630                 635                 640

Ile Leu Asp Tyr Asp Gln Ser Pro Ala Gly Cys Arg Asp Ala Leu Leu
            645                 650                 655

Gln Leu Thr Ser Gly Met Val Gln Thr His Val Thr Pro Gly Ser
            660                 665                 670

Ile Pro Thr Ile Cys Asp Leu Ala Arg Thr Phe Ala Arg Glu Met Gly
            675                 680                 685

Glu Ala Asn
    690

(2) INFORMATION FOR SEQ ID NO:3:

(i) SEQUENCE CHARACTERISTICS:
        (A) LENGTH: 2073 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..2073

(xi) SEQUENCE DESCRIPTION: SEQ ID NO:3:

ATG TCG AAT AAC GCT TTA CAA ACA ATT ATT AAC GCC CGG TTA CCA GGC     48
Met Ser Asn Asn Ala Leu Gln Thr Ile Ile Asn Ala Arg Leu Pro Gly
  1               5                  10                  15
```

```
GAA GAG GGG CTG TGG CAG ATT CAT CTG CAG GAC GGA AAA ATC AGC GCC      96
Glu Glu Gly Leu Trp Gln Ile His Leu Gln Asp Gly Lys Ile Ser Ala
            20                  25                  30

ATT GAT GCG CAA TCC GGC GTG ATG CCC ATA ACT GAA AAC AGC CTG GAT     144
Ile Asp Ala Gln Ser Gly Val Met Pro Ile Thr Glu Asn Ser Leu Asp
        35                  40                  45

GCC GAA CAA GGT TTA GTT ATA CCG CCG TTT GTG GAG CCA CAT ATT CAC     192
Ala Glu Gln Gly Leu Val Ile Pro Pro Phe Val Glu Pro His Ile His
    50                  55                  60

CTG GAC ACC ACG CAA ACC GCC GGA CAA CCG AAC TGG AAT CAG TCC GGC     240
Leu Asp Thr Thr Gln Thr Ala Gly Gln Pro Asn Trp Asn Gln Ser Gly
65                  70                  75                  80

ACG CTG TTT GAA GGC ATT GAA CGC TGG GCC GAG CGC AAA GCG TTA TTA     288
Thr Leu Phe Glu Gly Ile Glu Arg Trp Ala Glu Arg Lys Ala Leu Leu
                85                  90                  95

ACC CAT GAC GAT GTG AAA CAA CGC GCA TGG CAA ACG CTG AAA TGG CAG     336
Thr His Asp Asp Val Lys Gln Arg Ala Trp Gln Thr Leu Lys Trp Gln
            100                 105                 110

ATT GCC AAC GGC ATT CAG CAT GTG CGT ACC CAT GTC GAT GTT TCG GAT     384
Ile Ala Asn Gly Ile Gln His Val Arg Thr His Val Asp Val Ser Asp
        115                 120                 125

GCA ACG CTA ACT GCG CTG AAA GCA ATG CTG GAA GTG AAG CAG GAA GTC     432
Ala Thr Leu Thr Ala Leu Lys Ala Met Leu Glu Val Lys Gln Glu Val
    130                 135                 140

GCG CCG TGG ATT GAT CTG CAA ATC GTC GCC TTC CCT CAG GAA GGG ATT     480
Ala Pro Trp Ile Asp Leu Gln Ile Val Ala Phe Pro Gln Glu Gly Ile
145                 150                 155                 160

TTG TCG TAT CCC AAC GGT GAA GCG TTG CTG GAA GAG GCG TTA CGC TTA     528
Leu Ser Tyr Pro Asn Gly Glu Ala Leu Leu Glu Glu Ala Leu Arg Leu
                165                 170                 175

GGG GCA GAT GTA GTG GGG GCG ATT CCG CAT TTT GAA TTT ACC CGT GAA     576
Gly Ala Asp Val Val Gly Ala Ile Pro His Phe Glu Phe Thr Arg Glu
            180                 185                 190

TAC GGC GTG GAG TCG CTG CAT AAA ACC TTC GCC CTG GCG CAA AAA TAC     624
Tyr Gly Val Glu Ser Leu His Lys Thr Phe Ala Leu Ala Gln Lys Tyr
        195                 200                 205

GAC CGT CTC ATC GAC GTT CAC TGT GAT GAG ATC GAT GAC GAG CAG TCG     672
Asp Arg Leu Ile Asp Val His Cys Asp Glu Ile Asp Asp Glu Gln Ser
    210                 215                 220

CGC TTT GTC GAA ACC GTT GCT GCC CTG GCG CAC CAT GAA GGC ATG GGC     720
Arg Phe Val Glu Thr Val Ala Ala Leu Ala His His Glu Gly Met Gly
225                 230                 235                 240

GCG CGA GTC ACC GCC AGC CAC ACC ACG GCA ATG CAC TCC TAT AAC GGG     768
Ala Arg Val Thr Ala Ser His Thr Thr Ala Met His Ser Tyr Asn Gly
                245                 250                 255

GCG TAT ACC TCA CGC CTG TTC CGC TTG CTG AAA ATG TCC GGT ATT AAC     816
Ala Tyr Thr Ser Arg Leu Phe Arg Leu Leu Lys Met Ser Gly Ile Asn
            260                 265                 270

TTT GTC GCC AAC CCG CTG GTC AAT ATT CAT CTG CAA GGA CGT TTC GAT     864
Phe Val Ala Asn Pro Leu Val Asn Ile His Leu Gln Gly Arg Phe Asp
        275                 280                 285

ACG TAT CCA AAA CGT CGC GGC ATC ACG CGC GTT AAA GAG ATG CTG GAG     912
Thr Tyr Pro Lys Arg Arg Gly Ile Thr Arg Val Lys Glu Met Leu Glu
    290                 295                 300

TCC GGC ATT AAC GTC TGC TTT GGT CAC GAT GAT GTC TTC GAT CCG TGG     960
Ser Gly Ile Asn Val Cys Phe Gly His Asp Asp Val Phe Asp Pro Trp
305                 310                 315                 320

TAT CCG CTG GGA ACG GCG AAT ATG CTG CAA GTG CTG CAT ATG GGG CTG    1008
Tyr Pro Leu Gly Thr Ala Asn Met Leu Gln Val Leu His Met Gly Leu
```

```
                    325                 330                 335
CAT GTT TGC CAG TTG ATG GGC TAC GGG CAG ATT AAC GAT GGC CTG AAT        1056
His Val Cys Gln Leu Met Gly Tyr Gly Gln Ile Asn Asp Gly Leu Asn
            340                 345                 350

TTA ATC ACC CAC CAC AGC GCA AGG ACG TTG AAT TTG CAG GAT TAC GGC        1104
Leu Ile Thr His His Ser Ala Arg Thr Leu Asn Leu Gln Asp Tyr Gly
            355                 360                 365

ATT GCC GCC GGA AAC AGC GCC AAC CTG ATT ATC CTG CCG GCT GAA AAT        1152
Ile Ala Ala Gly Asn Ser Ala Asn Leu Ile Ile Leu Pro Ala Glu Asn
        370                 375                 380

GGG TTT GAT GCG CTG CGC CGT CAG GTT CCG GTA CGT TAT TCG GTA CGT        1200
Gly Phe Asp Ala Leu Arg Arg Gln Val Pro Val Arg Tyr Ser Val Arg
385                 390                 395                 400

GGC GGC AAG GTG ATT GCC AGC ACA CAA CCG GCA CAA ACC ACC GTA TAT        1248
Gly Gly Lys Val Ile Ala Ser Thr Gln Pro Ala Gln Thr Thr Val Tyr
                405                 410                 415

CTG GAG CAG CCA GAA GCC ATC GAT TAC AAA CGT ATT GAA CAA GAT GGA        1296
Leu Glu Gln Pro Glu Ala Ile Asp Tyr Lys Arg Ile Glu Gln Asp Gly
            420                 425                 430

TTG CAC GCA GGT TCT CCG GCC GCT TGG GTG GAG AGG CTA TTC GGC TAT        1344
Leu His Ala Gly Ser Pro Ala Ala Trp Val Glu Arg Leu Phe Gly Tyr
        435                 440                 445

GAC TGG GCA CAA CAG ACA ATC GGC TGC TCT GAT GCC GCC GTG TTC CGG        1392
Asp Trp Ala Gln Gln Thr Ile Gly Cys Ser Asp Ala Ala Val Phe Arg
450                 455                 460

CTG TCA GCG CAG GGG CGC CCG GTT CTT TTT GTC AAG ACC GAC CTG TCC        1440
Leu Ser Ala Gln Gly Arg Pro Val Leu Phe Val Lys Thr Asp Leu Ser
465                 470                 475                 480

GGT GCC CTG AAT GAA CTG CAG GAC GAG GCA GCG CGG CTA TCG TGG CTG        1488
Gly Ala Leu Asn Glu Leu Gln Asp Glu Ala Ala Arg Leu Ser Trp Leu
                485                 490                 495

GCC ACG ACG GGC GTT CCT TGC GCA GCT GTG CTC GAC GTT GTC ACT GAA        1536
Ala Thr Thr Gly Val Pro Cys Ala Ala Val Leu Asp Val Val Thr Glu
            500                 505                 510

GCG GGA AGG GAC TGG CTG CTA TTG GGC GAA GTG CCG GGG CAG GAT CTC        1584
Ala Gly Arg Asp Trp Leu Leu Leu Gly Glu Val Pro Gly Gln Asp Leu
        515                 520                 525

CTG TCA TCT CAC CTT GCT CCT GCC GAG AAA GTA TCC ATC ATG GCT GAT        1632
Leu Ser Ser His Leu Ala Pro Ala Glu Lys Val Ser Ile Met Ala Asp
530                 535                 540

GCA ATG CGG CGG CTG CAT ACG CTT GAT CCG GCT ACC TGC CCA TTC GAC        1680
Ala Met Arg Arg Leu His Thr Leu Asp Pro Ala Thr Cys Pro Phe Asp
545                 550                 555                 560

CAC CAA GCG AAA CAT CGC ATC GAG CGA GCA CGT ACT CGG ATG GAA GCC        1728
His Gln Ala Lys His Arg Ile Glu Arg Ala Arg Thr Arg Met Glu Ala
                565                 570                 575

GGT CTT GTC GAT CAG GAT GAT CTG GAC GAA GAG CAT CAG GGG CTC GCG        1776
Gly Leu Val Asp Gln Asp Asp Leu Asp Glu Glu His Gln Gly Leu Ala
            580                 585                 590

CCA GCC GAA CTG TTC GCC AGG CTC AAG GCG CGC ATG CCC GAC GGC GAG        1824
Pro Ala Glu Leu Phe Ala Arg Leu Lys Ala Arg Met Pro Asp Gly Glu
        595                 600                 605

GAT CTC GTC GTG ACC CAT GGC GAT GCC TGC TTG CCG AAT ATC ATG GTG        1872
Asp Leu Val Val Thr His Gly Asp Ala Cys Leu Pro Asn Ile Met Val
610                 615                 620

GAA AAT GGC CGC TTT TCT GGA TTC ATC GAC TGT GGC CGG CTG GGT GTG        1920
Glu Asn Gly Arg Phe Ser Gly Phe Ile Asp Cys Gly Arg Leu Gly Val
625                 630                 635                 640

GCG GAC CGC TAT CAG GAC ATA GCG TTG GCT ACC CGT GAT ATT GCT GAA        1968
```

```
Ala Asp Arg Tyr Gln Asp Ile Ala Leu Ala Thr Arg Asp Ile Ala Glu
            645                 650                 655

GAG CTT GGC GGC GAA TGG GCT GAC CGC TTC CTC GTG CTT TAC GGT ATC      2016
Glu Leu Gly Gly Glu Trp Ala Asp Arg Phe Leu Val Leu Tyr Gly Ile
            660                 665                 670

GCC GCT CCC GAT TCG CAG CGC ATC GCC TTC TAT CGC CTT CTT GAC GAG      2064
Ala Ala Pro Asp Ser Gln Arg Ile Ala Phe Tyr Arg Leu Leu Asp Glu
            675                 680                 685

TTC TTC TGA                                                          2073
Phe Phe
    690

(2) INFORMATION FOR SEQ ID NO:4:

(i) SEQUENCE CHARACTERISTICS:
        (A) LENGTH: 690 amino acids
        (B) TYPE: amino acid
        (D) TOPOLOGY: linear (ii) MOLECULE TYPE: protein (xi) SEQUENCE DESCRIPTION: SEQ ID NO:4:

Met Ser Asn Asn Ala Leu Gln Thr Ile Ile Asn Ala Arg Leu Pro Gly
  1               5                  10                  15

Glu Glu Gly Leu Trp Gln Ile His Leu Gln Asp Gly Lys Ile Ser Ala
                 20                  25                  30

Ile Asp Ala Gln Ser Gly Val Met Pro Ile Thr Glu Asn Ser Leu Asp
             35                  40                  45

Ala Glu Gln Gly Leu Val Ile Pro Pro Phe Val Glu Pro His Ile His
         50                  55                  60

Leu Asp Thr Thr Gln Thr Ala Gly Gln Pro Asn Trp Asn Gln Ser Gly
 65                  70                  75                  80

Thr Leu Phe Glu Gly Ile Glu Arg Trp Ala Glu Arg Lys Ala Leu Leu
                 85                  90                  95

Thr His Asp Asp Val Lys Gln Arg Ala Trp Gln Thr Leu Lys Trp Gln
                100                 105                 110

Ile Ala Asn Gly Ile Gln His Val Arg Thr His Val Asp Val Ser Asp
            115                 120                 125

Ala Thr Leu Thr Ala Leu Lys Ala Met Leu Glu Val Lys Gln Glu Val
        130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
                165                 170                 175

Gly Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
```

-continued

```
            275                 280                 285
Thr Tyr Pro Lys Arg Arg Gly Ile Thr Arg Val Lys Glu Met Leu Glu
    290                 295                 300
Ser Gly Ile Asn Val Cys Phe Gly His Asp Asp Val Phe Asp Pro Trp
305                 310                 315                 320
Tyr Pro Leu Gly Thr Ala Asn Met Leu Gln Val Leu His Met Gly Leu
                325                 330                 335
His Val Cys Gln Leu Met Gly Tyr Gly Gln Ile Asn Asp Gly Leu Asn
            340                 345                 350
Leu Ile Thr His His Ser Ala Arg Thr Leu Asn Leu Gln Asp Tyr Gly
                355                 360                 365
Ile Ala Ala Gly Asn Ser Ala Asn Leu Ile Ile Leu Pro Ala Glu Asn
            370                 375                 380
Gly Phe Asp Ala Leu Arg Arg Gln Val Pro Val Arg Tyr Ser Val Arg
385                 390                 395                 400
Gly Gly Lys Val Ile Ala Ser Thr Gln Pro Ala Gln Thr Thr Val Tyr
                405                 410                 415
Leu Glu Gln Pro Glu Ala Ile Asp Tyr Lys Arg Ile Glu Gln Asp Gly
            420                 425                 430
Leu His Ala Gly Ser Pro Ala Ala Trp Val Glu Arg Leu Phe Gly Tyr
            435                 440                 445
Asp Trp Ala Gln Gln Thr Ile Gly Cys Ser Asp Ala Ala Val Phe Arg
            450                 455                 460
Leu Ser Ala Gln Gly Arg Pro Val Leu Phe Val Lys Thr Asp Leu Ser
465                 470                 475                 480
Gly Ala Leu Asn Glu Leu Gln Asp Glu Ala Ala Arg Leu Ser Trp Leu
                485                 490                 495
Ala Thr Thr Gly Val Pro Cys Ala Ala Val Leu Asp Val Val Thr Glu
            500                 505                 510
Ala Gly Arg Asp Trp Leu Leu Leu Gly Glu Val Pro Gly Gln Asp Leu
            515                 520                 525
Leu Ser Ser His Leu Ala Pro Ala Glu Lys Val Ser Ile Met Ala Asp
    530                 535                 540
Ala Met Arg Arg Leu His Thr Leu Asp Pro Ala Thr Cys Pro Phe Asp
545                 550                 555                 560
His Gln Ala Lys His Arg Ile Glu Arg Ala Arg Thr Arg Met Glu Ala
                565                 570                 575
Gly Leu Val Asp Gln Asp Asp Leu Asp Glu Glu His Gln Gly Leu Ala
                580                 585                 590
Pro Ala Glu Leu Phe Ala Arg Leu Lys Ala Arg Met Pro Asp Gly Glu
            595                 600                 605
Asp Leu Val Val Thr His Gly Asp Ala Cys Leu Pro Asn Ile Met Val
            610                 615                 620
Glu Asn Gly Arg Phe Ser Gly Phe Ile Asp Cys Gly Arg Leu Gly Val
625                 630                 635                 640
Ala Asp Arg Tyr Gln Asp Ile Ala Leu Ala Thr Arg Asp Ile Ala Glu
                645                 650                 655
Glu Leu Gly Gly Glu Trp Ala Asp Arg Phe Leu Val Leu Tyr Gly Ile
                660                 665                 670
Ala Ala Pro Asp Ser Gln Arg Ile Ala Phe Tyr Arg Leu Leu Asp Glu
            675                 680                 685
Phe Phe
    690
```

(2) INFORMATION FOR SEQ ID NO:5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:5:

GCCGCCACCA TG                                                12

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:6:

GCTTAATTAA TTAAGC                                        16

(2) INFORMATION FOR SEQ ID NO:7:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (xi) SEQUENCE DESCRIPTION: SEQ ID NO:7:

GGATCGGCC                                                    9

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:8:

CCCGCTAGCC GCCACCATGT ACAGGATGCA ACTCC            35

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:9:

CCCGTCGACT TAATTATCAA GTCAGTGTT                  29

(2) INFORMATION FOR SEQ ID NO:10:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:10:

CTAGCCGCCA CCATGTCGAA TAACGCTTTA CAAACAATTA TTAACGCCCG      50

(2) INFORMATION FOR SEQ ID NO:11:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:11:

```
GTAACCGGGC GTTAATAATT GTTTGTAAAG CGTTATTCGA CATGGTGGCG G          51
```

(2) INFORMATION FOR SEQ ID NO:12:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:12:

```
CCCATCGATT ACAAACGTAA AAAGCCTGAA CTCACCGCGA C                     41
```

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:13:

```
GCCATGTAGT GTATTGACCG ATTCC                                       25
```

(2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:14:

```
ACTCTCGAAT AACGCTTTAC AAACAATTAT TAACGCCCG                        39
```

(2) INFORMATION FOR SEQ ID NO:15:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:15:

```
GTAACCGGGC GTTAATAATT GTTTGTAAAG CGTTATTCGA GAGT                  44
```

(2) INFORMATION FOR SEQ ID NO:16:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:16:

```
CGATTACAAA CGTATTGAAC AAGATGGATT GCACGCAGGT TCTCC                 45
```

(2) INFORMATION FOR SEQ ID NO:17:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:17:

GGCCGGAGAA CCTGCGTGCA ATCCATCTTG TTCAATACGT TTGTAAT                47

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:18:

CGAACTGTTC GCCAGGCTC                                               19

(2) INFORMATION FOR SEQ ID NO:19:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:19:

CCCGGTAACC GGGCGTTAAT AATTGTTTGT AAAGCGTTAT TCGAGAAGAA CTCGTCAAGA  60

AGGC                                                               64

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:20:

GTACAAGCTT GGATCCCTCG AGAT                                         24

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:21:

CGATCTCGAG GGATCCAAGC TT                                           22

(2) INFORMATION FOR SEQ ID NO:22:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:22:

CCCGCTAGCC GCCGCCACCA TGGGATCGGC CATTGAACAA GATGGATTGC AC          52

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:23:

CCCAAGCTTC CCGCTCAGAA GAACTCGTC                                              29

BIFUNCTIONAL SELECTABLE FUSION GENES

This application is a continuation, of application Ser. No. 08/066,388, filed May 21, 1993 now abandoned; wich is a continuation-in-part of U.S. Ser. No. 07/791,932, filed Nov. 12, 1991 (now abandoned); which is a continuation-in-part of U.S. Ser. No. 07/612,326, filed Nov. 13, 1990 (now abandoned).

BACKGROUND OF THE INVENTION

The present invention relates generally to genes expressing selectable phenotypes. More particularly, the present invention relates to genes capable of co-expressing both dominant positive selectable and negative selectable phenotypes.

Genes which express a selectable phenotype are widely used in recombinant DNA technology as a means for identifying and isolating host cells into which the gene has been introduced. Typically, the gene expressing the selectable phenotype is introduced into the host cell as part of a recombinant expression vector. Positive selectable genes provide a means to identify and/or isolate cells that have retained introduced genes in a stable form, and, in this capacity, have greatly facilitated gene transfer and the analysis of gene function. Negative selectable genes, on the other hand, provide a means for eliminating cells that retain the introduced gene.

A variety of genes are available which confer selectable phenotypes on animal cells. The bacterial neomycin phosphotransferase (neo) (Colbere-Garapin et al., *J. Mol. Biol.* 150:1, 1981), hygromycin phosphotransferase (hph) (Santerre et al., *Gene* 30:147, 1984), and xanthine-guanine phosphoribosyl transferase (gpt) (Mulligan and Berg, *Proc. Natl. Acad. Sci. USA* 78:2072, 1981) genes are widely used dominant positive selectable genes. The Herpes simplex virus type I thymidine kinase (HSV-I TK) gene (Wigler et al., *Cell* 11:223, 1977); the cellular adenine phosphoribosyltransferase (APRT) (Wigler et al., *Proc. Natl. Acad. Sci. USA* 76:1373, 1979); and hypoxanthine phosphoribosyltransferase (HPRT) genes (Jolly et al., *Proc. Natl. Acad. Sci. USA* 80:477, 1983) are commonly used recessive positive selectable genes. In general, dominant selectable genes are more versatile than recessive genes, because the use of recessive genes is limited to mutant cells deficient in the selectable function, whereas dominant genes may be used in wild-type cells.

Several genes confer negative as well as positive selectable phenotypes, including the HSV-I TK, HPRT, APRT and gpt genes. These genes encode enzymes which catalyze the conversion of nucleoside or purine analogs to cytotoxic intermediates. The nucleoside analog ganciclovir (GCV) is an efficient substrate for HSV-I TK, but a poor substrate for cellular TK, and therefore may be used for negative selection against the HSV-I TK gene in wild-type cells (St. Clair et al., *Antimicrob. Agents Chemother.* 31:844, 1987). However, the HSV-I TK gene may only be used effectively for positive selection in mutant cells lacking cellular TK activity. Use of the HPRT and APRT genes for either positive or negative selection is similarly limited to HPRT⁻ or APRT⁻ cells, respectively (Fenwick, "The HGPRT System", pp. 333–373, M. Gottesman (ed.), *Molecular Cell Genetics*, John Wiley and Sons, New York, 1985; Taylor et al., "The APRT System", pp. 311–332, M. Gottesman (ed.), *Molecular Cell Genetics*, John Wiley and Sons, New York, 1985). The gpt gene, on the other hand, may be used for both positive and negative selection in wild-type cells. Negative selection against the gpt gene in wild-type cells is possible using 6-thioxanthine, which is efficiently converted to a cytotoxic nucleotide analog by the bacterial gpt enzyme, but not by the cellular HPRT enzyme (Besnard et al., *Mol. Cell. Biol.* 7:4139, 1987).

Another negatively selectable gene has recently been reported by Mullen et al., *Proc. Natl. Acad. Sci. USA* 89:33, 1992. The bacterial cytosine deaminase (CD) gene converts 5-fluorocytosine (5-FC) to 5-fluorouracil (5-FU). 5-FU is further metabolized intracellularly to 5-fluoro-uridine-5'-triphosphate and 5-fluoro-2'-deoxy-uridine-5'-monophosphate, which inhibit RNA and DNA synthesis, causing cell death. Thus, 5-FC can effectively ablate cells carrying and expressing the CD gene. The CD gene is not positively selectable in normal cells.

More recently, attention has turned to selectable genes that may be incorporated into gene transfer vectors designed for use in human gene therapy. Gene therapy can be used as a means for augmenting normal gene function, for example, by introducing a heterologous gene capable of modifying cellular activities or cellular phenotype, or alternatively, expressing a drug needed to treat a disease. Gene therapy also is a method for permanently curing a hereditary genetic disease which results from a defect in or absence of one or more genes. Collectively, such diseases result in significant morbidity and mortality. Examples of such genetic diseases include hemophilias A and B (caused by a deficiency of blood coagulation factors VIII and IX, respectively), alpha-1-antitrypsin deficiency, and adenosine deaminase deficiency. In each of these particular cases, the missing gene has been identified and its complementary DNA (cDNA) molecularly cloned (Wood et al., *Nature* 312:330, 1984; Anson et al., *Nature* 315:683, 1984; and Long et al., *Biochemistry* 23:4828, 1984; Daddona et al., *J. Biol. Chem.* 259:12101, 1984). While palliative therapy is available for some of these genetic diseases, often in the form of administration of blood products or blood transfusions, one way of permanently curing such genetic diseases is to introduce a replacement for the defective or missing gene back into the somatic cells of the patient, a process referred to as "gene therapy" (Anderson, *Science* 226:401, 1984).

The process of gene therapy typically involves the steps of (1) removing somatic (non-germ) cells from the patient, (2) introducing into the cells ex vivo a therapeutic or replacement gene via an appropriate vector capable of expressing the therapeutic or replacement gene, and (3) transplanting or transfusing these cells back into the patient, where the therapeutic or replacement gene is expressed to provide some therapeutic benefit. Gene transfer into somatic cells for human gene therapy is presently achieved ex vivo (Kasid et al., *Proc. Natl. Acad. Sci. USA* 87:473, 1990; Rosenberg et al., *N. Engl. J. Med.* 323:570, 1990), and this relatively inefficient process would be facilitated by the use of a dominant positive selectable gene for identifying and isolating those cells into which the replacement gene has been introduced before they are returned to the patient. The neo gene, for example, has been used to identify genetically modified cells used in human gene therapy.

In some instances, however, it is possible that the introduction of genetically modified cells may actually compromise the health of the patient. The ability to selectively eliminate genetically modified cells in vivo would provide an additional margin of safety for patients undergoing gene therapy, by permitting reversal of the procedure. This might be accomplished by incorporating into the vector a negative selectable (or "suicide") gene that is capable of functioning in wild-type cells. Incorporation of a gene capable of conferring both dominant positive and negative selectable phenotypes would ensure co-expression and co-regulation of the positive and negative selectable phenotypes, and would minimize the size of the vector. However, positive selection for the gpt gene in some instances requires precise selection conditions which may be difficult to determine. Moreover, the feasibility of using the gpt gene for in vivo negative selection has not yet been clearly established. For these reasons, co-expression of a dominant positive selectable phenotype and a negative selectable phenotype is typically achieved by co-expressing two different genes which separately encode other dominant positive and negative selectable functions, rather than using the gpt gene.

The existing strategies for co-expressing dominant positive and negative selectable phenotypes encoded by different genes often present complex challenges. As indicated above, the most widely used technique is to co-transfect two plasmids separately encoding two phenotypes (Wigler et al., *Cell* 16:777, 1979). However, the efficiency of co-transfer is rarely 100%, and the two genes may be subject to independent genetic or epigenetic regulation. A second strategy is to link the two genes on a single plasmid, or to place two independent transcription units into a viral vector. This method also suffers from the disadvantage that the genes may be independently regulated. In retroviral vectors, suppression of one or the other independent transcription unit may occur (Emerman and Temin, *Mol.Cell. Biol.* 6:792, 1986). In addition, in some circumstances there may be insufficient space to accommodate two functional transcription units within a viral vector, although retroviral vectors with functional multiple promoters have been successfully made (Overell et al., *Mol. Cell. Biol.* 8:1803, 1988). A third strategy is to express the two genes as a bicistronic mRNA using a single promoter. With this method, however, the distal open reading frame is often translated with variable (and usually reduced) efficiency (Kaufman et al., *EMBO J.* 6:187, 1987), and it is unclear how effective such an expression strategy would be in primary cells.

The present invention provides a method for more efficiently and reliably co-expressing a dominant positive selectable phenotype and a negative selectable phenotype encoded by different genes.

SUMMARY OF THE INVENTION

The present invention provides a selectable fusion gene comprising a dominant positive selectable gene fused to and in reading frame with a negative selectable gene. The selectable fusion gene encodes a single bifunctional fusion protein which is capable of conferring a dominant positive selectable phenotype and a negative selectable phenotype on a cellular host. In a preferred embodiment, the selectable fusion gene comprises nucleotide sequences from the hph gene fused to nucleotide sequences from the HSV-I TK gene, referred to herein as the HyTK selectable fusion gene (SEQ ID NO:1. The HyTK selectable fusion gene confers both hygromycin B resistance ($Hm^r$) for dominant positive selection and ganciclovir sensitivity ($GCV^s$) for negative selection.

In another preferred embodiment, the selectable fusion gene comprises nucleotide sequences from the bacterial CD gene fused to nucleotide sequences from the neo gene, referred to herein as the CD-neo selectable fusion gene (SEQ ID NO:3. The CD-neo selectable fusion gene confers both G-418 resistance ($G-418^r$) for dominant positive selection and 5-fluorocytosine sensitivity ($5-FC^s$) for negative selection.

The present invention also provides recombinant expression vectors, for example, retroviruses, which include the selectable fusion genes, and cells transduced with the recombinant expression vectors.

The selectable fusion genes of the present invention are expressed and regulated as a single genetic entity, permitting co-regulation and co-expression with a high degree of efficiency.

BRIEF DESCRIPTION OF THE DRAWINGS

FIG. 3 shows that GCV inhibits growth of NIH/3T3 cells transfected with tgCMV/HyTK, but does not inhibit growth of NIH/3T3 cells transfected with tgCMV/hygro. FIG. 4 shows that GCV inhibits growth of Rat-2 cells transfected with tgCMV/HyTK (initially selected for $Hm^r$ or $HAT^r$) even at the lowest concentrations of GCV, and also inhibits growth of Rat-2 cells transfected with tgCMV/TK, although at slightly higher concentrations. GCV did not inhibit growth of Rat-2 cells transfected with tgCMV/hygro.

FIGS. 2a–2g show photographs of stained colonies of uninfected NIH/3T3 cells (plates a, b and c) and NIH/3T3 cells infected with the tgLS(+)neo (plates d and e) or tgLS(+)CD-neo (plates f and g) retroviruses. The cells were grown in medium alone (plate a) or medium supplemented with G-418 (plates b, d and f), 5-FC (plate c) or G-418 and 5-FC (plates e and g) in a long-term proliferation assay. The data'show that uninfected NIH/3T3 cells were sensitive to G-418 and resistant to 5-FC, NIH/3T3 cells infected with tgLS(+)neo are resistant to both G-418 and 5-FC, and NIH/3T3 cells infected with tgLS(+)CD-neo are resistant to G-418 and sensitive to 5-FC.

DETAILED DESCRIPTION OF THE INVENTION

Figure 1:
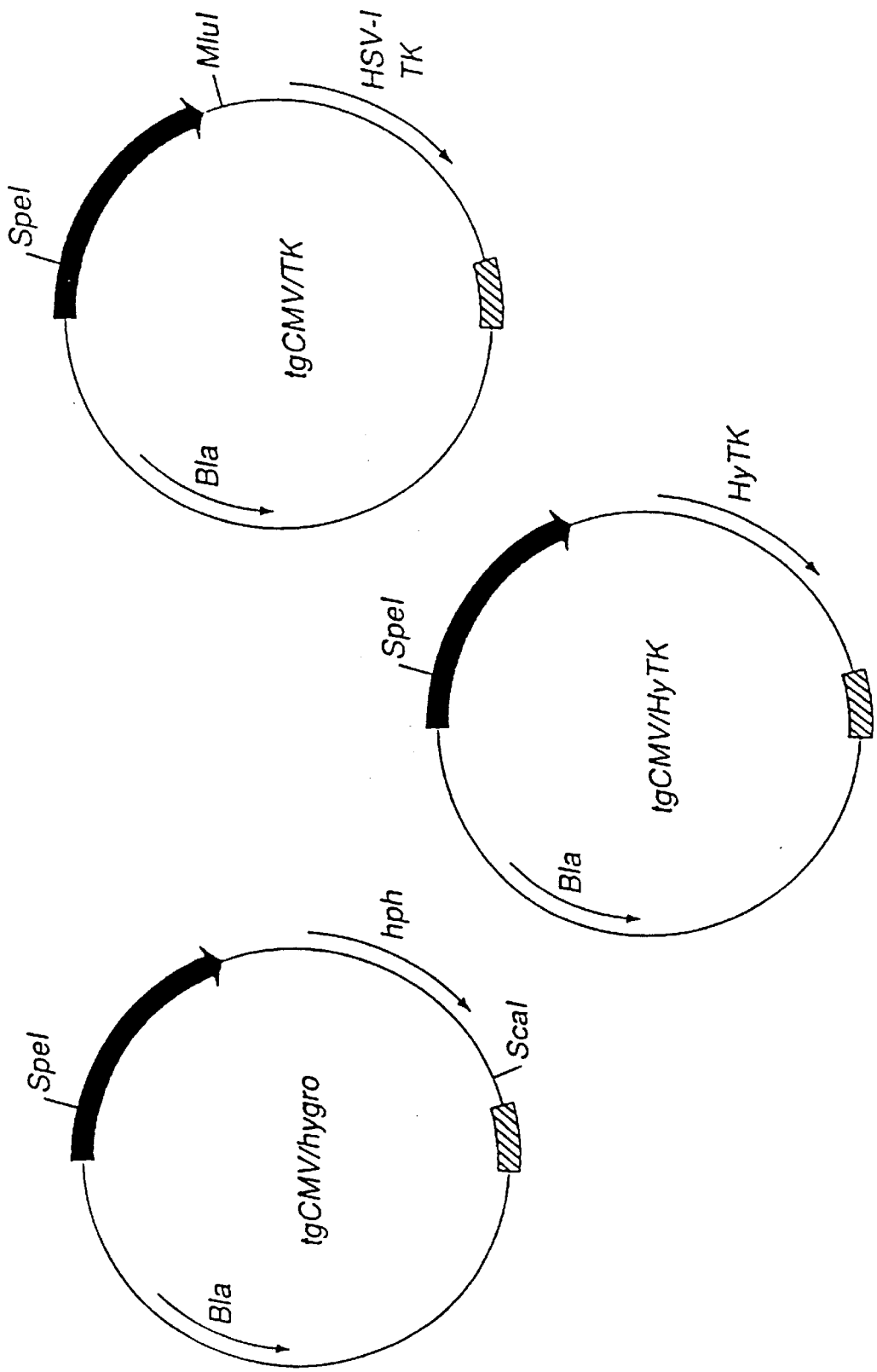
FIG. 1 shows diagrams of the plasmids tgCMV/hygro, tgCMV/TK and tgCMV/HyTK used in the present invention. The three plasmids are identical, except for the genes inserted between the HCMV promoter (filled box) and the SV40 early region polyadenylation signal (hatched box).

SEQ ID NO:1 and SEQ ID NO:2 (appearing immediately prior to the claims) show specific embodiments of the nucleotide sequence and corresponding amino acid sequence of the HyTK (SEQ ID NO:1 selectable fusion gene of the present invention. The HyTK (SEQ ID NO:1 selectable fusion gene shown in the Sequence Listing comprises sequences from the hph gene (nucleotides 1–971) linked to sequences from the HSV-I TK gene (nucleotides 972–2076). SEQ ID NO:3 and SEQ ID NO:4 show specific embodiments of the nucleotide sequence and corresponding amino acid sequence of the CD-neo (SEQ ID NO:3 selectable fusion genes of the present invention. The CD-neo (SEQ ID NO:3 selectable fusion gene shown in the Sequence Listing comprises sequences from the CD gene (nucleotides 4–1281) linked to sequences from the neo gene (nucleotides 1282–2073).

Definitions

As used herein, the term "selectable fusion gene" refers to a nucleotide sequence comprising a dominant positive selectable gene which is fused to and in reading frame with a negative selectable gene and which encodes a single bifunctional fusion protein which is capable of conferring a dominant positive selectable phenotype and a negative selectable phenotype on a cellular host. A "dominant positive selectable gene" refers to a sequence of nucleotides which encodes a protein conferring a dominant positive selectable phenotype on a cellular host, and is discussed and exemplified in further detail below. A "negative selectable gene" refers to a sequence of nucleotides which encodes a protein conferring a negative selectable phenotype on a cellular host, and is also discussed and exemplified in further detail below. A "selectable gene" refers generically to dominant positive selectable genes and negative selectable genes.

A selectable gene is "fused to and in reading frame with" another selectable gene if the expression products of the selectable genes (i.e., the proteins encoded by the selectable genes) are fused by a peptide bond and at least part of the biological activity of each of the two proteins is retained. With reference to the HyTK (SEQ ID NO:1 selectable fusion gene disclosed herein, for example, the hph gene (encoding hygromycin-B phosphotransferase, which confers the dominant positive selectable phenotype of hygromycin resistance (Hm$^r$)) is fused to and in reading frame with the HSV-I TK gene (encoding Herpes Simplex Virus Type I thymidine kinase, which confers a negative selectable phenotype of ganciclovir sensitivity, or (GCV$^s$)) if the hph and HSV-I TK proteins are fused by a peptide bond and expressed as a single bifunctional fusion protein.

With reference to the CD-neo (SEQ ID NO:3 selectable fusion gene disclosed herein, the CD gene (encoding the cytosine deaminase, which confers a negative selectable phenotype of 5-fluorocytosine sensitivity, or 5-FC$^s$) is fused to and in reading frame with the neo gene (encoding neomycin phosphotransferase, which confers the dominant positive selectable phenotype of G-418 resistance, or G-418$^r$) if the CD and neo proteins are fused by a peptide bond and expressed as a single bifunctional fusion protein.

The component selectable gene sequences of the present invention are preferably contiguous; however, it is possible to construct selectable fusion genes in which the component selectable gene sequences are separated by internal non-translated nucleotide sequences, such as introns. For purposes of the present invention, such noncontiguous selectable gene sequences are considered to be fused, provided that expression of the selectable fusion gene results in a single bifunctional fusion protein in which the expression products of the component selectable gene sequences are fused by a peptide bond.

"Nucleotide sequence" refers to a heteropolymer of deoxyribonucleotides or ribonucleotides, such as a DNA or RNA sequence. Nucleotide sequences may be in the form of a separate fragment or as a component of a larger construct. Preferably, the nucleotide sequences are in a quantity or concentration enabling identification, manipulation, and recovery of the sequence by standard biochemical methods, for example, using a cloning vector. Recombinant nucleotide sequences are the product of various combinations of cloning, restriction, and ligation steps resulting in a construct having a structural coding sequence distinguishable from homologous sequences found in natural systems. Generally, nucleotide sequences encoding the structural coding sequence, for example, the selectable fusion genes of the present invention, can be assembled from nucleotide fragments and short oligonucleotide linkers, or from a series of oligonucleotides, to provide a synthetic gene which is capable of being expressed in a recombinant transcriptional unit. Such sequences are preferably provided in the form of an open reading frame uninterrupted by internal nontranslated sequences, or introns, which are typically present in eukaryotic genes. Genomic DNA containing the relevant selectable gene sequences is preferably used to obtain appropriate nucleotide sequences encoding selectable genes; however, cDNA fragments may also be used. Sequences of non-translated DNA may be present 5' or 3' from the open reading frame or within the open reading frame, provided such sequences do not interfere with manipulation or expression of the coding regions. Some genes, however, may include introns which are necessary for proper expression in certain hosts, for example, the HPRT selectable gene includes introns which are necessary for expression in embryonal stem (ES) cells. As suggested above, the nucleotide sequences of the present invention may also comprise RNA sequences, for example, where the nucleotide sequences are packaged as RNA in a retrovirus for infecting a cellular host. The use of retroviral expression vectors is discussed in greater detail below.

The term "recombinant expression vector" refers to a replicable unit of DNA or RNA in a form which is capable of being transduced into a target cell by transfection or viral infection, and which codes for the expression of a selectable fusion gene which is transcribed into mRNA and translated into protein under the control of a genetic element or elements having a regulatory role in gene expression, such as transcription and translation initiation and termination sequences. The recombinant expression vectors of the present invention can take the form of DNA constructs replicated in bacterial cells and transfected into target cells directly, for example, by calcium phosphate precipitation, electroporation or other physical transfer methods. The recombinant expression vectors which take the form of RNA constructs may, for example, be in the form of infectious retroviruses packaged by suitable "packaging" cell lines which have previously been transfected with a proviral DNA vector and produce a retrovirus containing an RNA transcript of the proviral DNA. A host cell is infected with the retrovirus, and the retroviral RNA is replicated by reverse transcription into a double-stranded DNA intermediate which is stably integrated into chromosomal DNA of the host cell to form a provirus. The provirus DNA is then expressed in the host cell to produce polypeptides encoded by the DNA. The recombinant expression vectors of the present invention thus include not only RNA constructs present in the infectious retrovirus, but also copies of proviral DNA, which include DNA reverse transcripts of a retrovirus RNA genome stably integrated into chromosomal DNA in a suitable host cell, or cloned copies thereof, or cloned copies of unintegrated intermediate forms of retroviral DNA. Proviral DNA includes transcriptional elements in independent operative association with selected structural DNA sequences which are transcribed into mRNA and translated into protein when proviral sequences are expressed in infected host cells. Recombinant expression vectors used for direct transfection will include DNA sequences enabling replication of the vector in bacterial host cells. Various recombinant expression vectors suitable for use in the present invention are described below.

"Transduce" means introduction of a recombinant expression vector containing a selectable fusion gene into a cell. Transduction methods may be physical in nature (i.e., transfection), or they may rely on the use of recombinant viral vectors, such as retroviruses, encoding DNA which can be transcribed to RNA, packaged into infectious viral particles and used to infect target cells and thereby deliver the desired genetic material (i.e., infection). Many different types of mammalian gene transfer and recombinant expression vectors have ben developed (see, e.g., Miller and Calos, Eds., "Gene Transfer Vectors for Mammalian Cells," *Current Comm. Mol. Biol.*, (Cold Spring Harbor Laboratory, New York, 1987)). Naked DNA can be physically introduced into mammalian cells by transfection using any one of a number of techniques including, but not limited to, calcium phosphate transfection (Berman et al., *Proc. Natl. Acad. Sci. USA* 84 81:7176, 1984), DEAE-Dextran transfection (McCutchan et al., *J. Natl. Cancer Inst.* 41:351, 1986; Luthman et al., *Nucl. Acids Res.* 11:1295, 1983), protoplast fusion (Deans et al., *Proc. Natl. Acad. Sci. USA* 84 81:1292, 1984), electroporation (Potter et al., *Proc. Natl. Acad. Sci. USA* 84 81:7161, 1984), lipofection (Felgner et al., *Proc. Natl. Acad. Sci. USA* 84:7413, 1987), Polybrene hexadimethrine bromide transfection (Kawai and Nishizawa, *Mol. Cell. Biol.* 4:1172, 1984) and direct gene transfer by laser micropuncture of cell membranes.(Tao et al., *Proc. Natl. Acad. Sci. USA* 84:4180, 1987). Various infection techniques have been developed which utilize recombinant infectious virus particles for gene delivery. This represents a preferred approach to the present invention. The viral vectors which have been used in this way include virus vectors derived from simian virus 40 (SV40; Karlsson et al., *Proc. Natl. Acad. Sci. USA* 84 82:158, 1985), adenoviruses (Karlsson et al., *EMBO J.* 5:2377, 1986), adeno-associated virus (LaFace et al., *Virology* 162:483, 1988) and retroviruses (Coffin, 1985, p17–71 in Weiss et al. (eds.), *RNA Tumor Viruses*, 2nd ed. Vol 2, Cold Spring Harbor Laboratory, New York). Thus, gene transfer and expression methods are numerous but essentially function to introduce and express genetic material in mammalian cells. Several of the above techniques have been used to transduce hematopoietic or lymphoid cells, including calcium phosphate transfection (Berman et al., supra, 1984), protoplast fusion (Deans et al., supra, 1984), electroporation (Cann et al., *Oncogene* 3:123, 1988), and infection with recombinant adenovirus (Karlsson et al., supra; Reuther et al., *Mol. Cell. Biol.* 6:123, 1986) adeno-associated virus (LaFace et al., supra) and retrovirus vectors (Overell et al., *Oncogene* 4:1425, 1989). Primary T lymphocytes have been successfully transduced by electroporation (Cann et al., supra, 1988) and by retroviral infection (Nishihara et al., *Cancer Res.* 48:4730, 1988; Kasid et al., supra, 1990).

Construction of Selectable Fusion Genes

The selectable fusion genes of the present invention comprise a dominant positive selectable gene fused to a negative selectable gene. A selectable gene will generally comprise, for example, a gene encoding a protein capable of conferring an antibiotic resistance phenotype or supplying an autotrophic requirement (for dominant positive selection), or activating a toxic metabolite (for negative selection). A DNA sequence encoding a bifunctional fusion protein is constructed using recombinant DNA techniques to assemble separate DNA fragments encoding a dominant positive selective gene and a negative selectable gene into an appropriate expression vector. The 3' end of the one selectable gene is ligated to the 5' end of the other selectable gene, with the reading frames of the sequences in frame to permit translation of the mRNA sequences into a single biologically active bifunctional fusion protein. The selectable fusion gene is expressed under control of a single promoter.

The dominant positive selectable gene is any gene which, upon being transduced into a host cell, expresses a dominant phenotype permitting positive selection of stable transductants. Selection of stable transductants can be carried out, for example, using the hygromycin-B phosphotransferase gene (hph) which confers the selectable phenotype of hygromycin resistance (Hm$^r$) (Santerre et al., *Gene* 30:147, 1984; Sugden et al., *Mol. Cell. Biol.* 5:410, 1985; obtainable from plasmid pHEBol, under ATCC Accession No. 39820). Hygromycin B is an aminoglycoside antibiotic that inhibits protein synthesis by disrupting translocation and promoting mistranslation. The hph gene confers Hm$^r$ to cells transduced with the hph gene by phosphorylating and detoxifying the antibiotic hygromycin B. Other acceptable dominant positive selectable genes include the following: the aminoglycoside phosphotransferase gene (neo or aph) from Tn5 which codes for resistance to the antibiotic G418 (Colbere-Garapin et al., *J. Mol. Biol.* 150:1, 1981; Southern and Berg, *J. Mol. Appl. Genet.* 1:327, 1982); the xanthine-guanine phosphoribosyl transferase gene (gpt) from *E. coli* encoding resistance to mycophenolic acid (Mulligan and Berg, *Proc. Natl. Acad. Sci. USA* 78:2072, 1981); the dihydrofolate reductase (DHFR) gene from murine cells or *E. coli* which is necessary for biosynthesis of purines and can be competitively inhibited by the drug methotrexate (MTX) to select for cells constitutively expressing increased levels of DHFR (Simonsen and Levinson, *Proc. Natl. Acad. Sci. USA* 80:2495, 1983; Simonsen et al., *Nucl. Acids Res.* 16:2235, 1988); the *S. typhimurium* histidinol dehydrogenase (hisD) gene (Hartman et al., *Proc. Natl. Acad. Sci. USA* 85:8047, 1988); the *E. coli* tryptophan synthase β subunit (trpB) gene (Hartman et al., supra); the puromycin-N-acetyl transferase (pac) gene (Vara et al., *Nucl. Acids Res.* 14:4117, 1986); the adenosine deaminase (ADA) gene (Daddona et al., *J. Biol. Chem.* 259:12101, 1984); the multi-drug resistance (MDR) gene (Kane et al., *Gene* 84:439, 1989); the mouse ornithine decarboxylase (OCD) gene (Gupba and Coffino, *J. Biol. Chem.* 160:2941, 1985); the *E. coli* aspartate transcarbamylase catalytic subunit (pyrB) gene (Ruiz and Wahl, *Mol. Cell. Biol.* 6:3050, 1986); and the *E. coli* asnA gene, encoding asparagine synthetase (Cartier et al., *Mol. Cell. Biol.* 7:1623, 1987).

The negative selectable gene is any gene which, upon being transduced into a host cell, expresses a phenotype permitting negative selection (i.e., elimination) of stable transductants. In preferred embodiments, the negative selectable genes used in the fusion genes of the present invention are the Herpes simplex virus type I thymidine kinase (HSV-I TK) gene (Wigler et al., *Cell* 11:223, 1977; McKnight et al., *Nucl. Acids Res.* 8:5931, 1980; Preston et al., *J. Virol.* 38:593, 1981; Wagner et al., *Proc. Natl. Acad. Sci. USA* 78:1441, 1981) and Varicella zoster virus thymidine kinase (VZV TK) gene (Davison & Scott, *J. Gen. Virol.* 67:1759, 1986) which confers ganciclovir sensitivity (GCV$^s$) (St. Clair et al., *Antimicrob. Agents Chemother.* 31:844, 1987). The HSV-I TK gene is available from Bethesda Research Labs (Catalog No. BRL 5365 SA). Another embodiment is the bacterial CD gene encoding cytosine deaminase (Genbank accession number X63656) which confers 5-fluorocytosine sensitivity.

Negative selection can also be performed, for example, using the cellular hypoxanthine phosphoribosyltransferase (HPRT) gene (Jolly et al., *Proc. Natl. Acad. Sci. USA* 80:477, 1983; Fenwick, "The HGPRT System", pp. 333–373, M. Gottesman (ed.), *Molecular Cell Genetics*, (John Wiley and Sons, New York, 1985)); the cellular adenine phosphoribosyltransferase (APRT) gene (Wigler et al., *Proc. Natl. Acad. Sci. USA* 76:1373, 1979; Taylor et al., "The APRT System", pp. 311–332, M. Gottesman (ed.), *Molecular Cell Genetics*, (John Wiley and Sons, New York, 1985)); and the *E. coli* gpt gene (Besnard et al., *Mol. Cell. Biol.* 7:4139, 1987)

Other enzymes suitable for negative selection include, but are not limited to, alkaline phosphatase useful for converting phosphate-containing prodrugs such as etoposide-phosphate, doxorubicin-phosphate, mitomycin phosphate, into toxic dephosphorylated metabolites; arylsulfatase useful for converting sulfate-containing prodrugs into free drugs; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amino nitrogens with phenoxyacetyl or phenylacetyl groups, respectively, into free drugs.

Other enzyme prodrug combinations include the bacterial (for example, from Pseudomonas) enzyme carboxypeptidase G2 with the prodrug para-N-bis(2-chloroethyl) aminobenzoyl glutamic acid. Cleavage of the glutamic acid moiety from this compound releases a toxic benzoic acid mustard. Penicillin-V amidase will convert phenoxyacetamide derivatives of doxorubicin and melphalan to toxic metabolites.

Due to the degeneracy of the genetic code, there can be considerable variation in nucleotide sequences encoding the same amino acid sequence; exemplary DNA embodiments are those corresponding to the nucleotide sequences in (SEQ ID NO:1. Such variants will have modified DNA or amino acid sequences, having one or more substitutions, deletions, or additions, the net effect of which is to retain biological activity, and may be substituted for the specific sequences disclosed herein. The sequences of selectable fusion genes comprising hph and TK are equivalent if they contain all or part of the sequences of hph and HSV-I TK and are capable of hybridizing to the nucleotide sequence of (SEQ ID NO:1 under moderately stringent conditions (50° C., 2 X SSC) and express a biologically active fusion protein. Likewise, the sequences of selectable fusion genes comprising CD and neo are equivalent if they contain all or part of the sequences of CD and neo and are capable of hybridizing to the nucleotide sequence of (SEQ ID NO:1 under moderately stringent conditions and express a biologically active fusion protein.

A "biologically active" fusion protein will share sufficient amino acid sequence similarity with the specific embodiments of the present invention disclosed herein to be capable of conferring the selectable phenotypes of the component selectable genes.

In a preferred embodiment, sequences from the bacterial hygromycin phosphotransferase (hph) gene are fused with sequences from the HSV-I TK gene. The resulting selectable fusion gene (referred to as the HyTKR (SEQ ID NO:1 selectable fusion gene) encodes a bifunctional fusion protein that confers Hm$^r$ and GCV$^s$, and provides a means by which dominant positive and negative selectable phenotypes may be expressed and regulated as a single genetic entity. The HyTK (SEQ ID NO:1 selectable fusion gene is therefore a useful addition to the existing panel of selectable genes available for use in animal cells, because it allows both dominant positive and negative selection in wild-type cells.

In another preferred embodiment, sequences from the bacterial cytosine deaminase (CD) gene are fused with sequences from the bacterial neomycin phosphotransferase (neo) gene. The resulting selectable fusion gene (referred as the CD-neo (SEQ ID NO:3 selectable fusion gene) encodes a bifunctional fusion protein that confers G-418$^r$ and 5-GC$^s$ and provides a means by which dominant positive and negative selectable phenotypes may be expressed and regulated as a single genetic entity. The CD-neo (SEQ ID NO:3 selectable fusion gene is also a useful addition to the existing panel of selectable genes and may be preferred to the HyTK (SEQ ID NO:1 gene in patient populations likely to receive ganciclovir.

Recombinant Expression Vectors

The selectable fusion genes of the present invention are utilized to identify, isolate or eliminate host cells into which the selectable fusion genes are introduced. The selectable fusion genes are introduced into the host cell by transducing into the host cell a recombinant expression vector which contains the selectable fusion gene. Such host cells include cell types from higher eukaryotic origin, such as mammalian or insect cells, or cell types from lower prokaryotic origin, such as bacterial cells, for example, E. coli.

As indicated above, such selectable fusion genes are preferably introduced into a particular cell as a component of a recombinant expression vector which is capable of expressing the selectable fusion gene within the cell and conferring a selectable phenotype. Such recombinant expressionvectors generally include synthetic or natural nucleotide sequences comprising the selectable fusion gene operably linked to suitable transcriptional or translational control sequences, for example, an origin of replication, optional operator sequences to control transcription, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Such regulatory sequences can be derived from mammalian, viral, microbial or insect genes. Nucleotide sequences are operably linked when they are functionally related to each other. For example, a promoter is operably linked to a selectable fusion gene if it controls the transcription of the selectable fusion gene; or a ribosome binding site is operably linked to a selectable fusion gene if it is positioned so as to permit translation of the selectable fusion gene into a single bifunctional fusion protein. Generally, operably linked means contiguous.

Specific recombinant expression vectors for use with mammalian, bacterial, and yeast cellular hosts are described by Pouwels et al. (*Cloning Vectors: A Laboratory Manual*, Elsevier, N.Y., 1985) and are well-known in the art. A detailed description of recombinant expression vectors for use in animal cells can be found in Rigby, *J. Gen. Virol.* 64:255, 1983); Elder et al., *Ann. Rev. Genet.* 15:295, 1981; and Subramani et al., *Anal. Biochem.* 135:1, 1983. Appropriate recombinant expression vectors may also include viral vectors, in particular retroviruses (discussed in detail below).

The selectable fusion genes of the present invention are preferably placed under the transcriptional control of a strong enhancer and promoter expression cassette. Examples of such expression cassettes include the human cytomegalovirus immediate-early (HCMV-IE) promoter (Boshart et al., *Cell* 41:521, 1985), the β-actin promoter (Gunning et al., *Proc. Natl. Acad. Sci. USA* 84:5831, 1987), the histone H4 promoter (Guild et al., *J. Virol.* 62:3795, 1988), the mouse metallothionein promoter (McIvor et al., *Mol. Cell. Biol.* 7:838, 1987), the rat growth hormone promoter (Miller et al., *Mol. Cell Biol.* 5:431, 1985), the human adenosine deaminase promoter (Hantzapoulos et al., *Proc. Natl. Acad. Sci. USA* 86:3519, 1989) the HSV TK promoter (Tabin et al., *Mol. Cell. Biol.* 2:426, 1982), the α-1 antitrypsin enhancer (Peng et al., *Proc. Natl. Acad. Sci. USA* 85:8146, 1988) and the immunoglobulin enhancer/promoter (Blankenstein, et al., *Nucleic Acid Res.* 16:10939, 1988), the SV40 early or late promoters, the Adenovirus 2 major late promoter, or other viral promoters derived from polyoma virus, bovine papilloma virus, or other retroviruses or adenoviruses. The promoter and enhancer elements of immunoglobulin (Ig) genes confer marked specificity to B lymphocytes (Banerji et al., *Cell* 33:729, 1983; Gillies et al., *Cell* 33:717, 1983; Mason et al., *Cell* 41:479, 1985), while the elements controlling transcription of the β-globin gene function only in erythroid cells (van Assendelft et al., *Cell* 56:969, 1989). Using well-known restriction and ligation techniques, appropriate transcriptional control sequences can be excised from various DNA sources and integrated in operative relationship with the intact selectable fusion genes to be expressed in accordance with the present invention. Thus, many transcriptional control sequences may be used successfully in retroviral vectors to direct the expression of inserted genes in infected cells.

Retroviruses

Retroviruses can be used for highly efficient transduction of the selectable fusion genes of the present invention into eukaryotic cells and are preferred for the delivery of a selectable fusion gene into primary cells. Moreover, retroviral integration takes place in a controlled fashion and results in the stable integration of one or a few copies of the new genetic information per cell.

Retroviruses are a class of viruses whose genome is in the form of RNA. The genomic RNA of a retrovirus contains trans-acting gene sequences coding for three viral proteins: a structural protein gag which associates with the RNA in the core of the virus particle; the reverse transcriptase pol which makes the DNA complement; and an envelope glycoprotein env which resides in the lipoprotein envelope of the particles and binds the virus to the surface of host cells on infection. Replication of the retrovirus is regulated by cis-acting elements, such as the promoter for transcription of the proviral DNA and other nucleotide sequences necessary for viral replication. The cis-acting elements are present in or adjacent to two identical untranslated long terminal repeats (LTRs) of about 600 base pairs present at the 5' and 3' ends of the retroviral genome. Retroviruses replicate by copying their RNA genome by reverse transcription into a double-stranded DNA intermediate, using a virus-encoded, RNA-directed DNA polymerase, or reverse transcriptase. The DNA intermediate is integrated into chromosomal DNA of an avian or mammalian host cell. The integrated retroviral DNA is called a provirus. The provirus serves as template for the synthesis of RNA chains for the formation of infectious virus particles. Forward transcription of the provirus and assembly into infectious virus particles occurs in the presence of an appropriate helper virus having endogenous trans-acting genes required for viral replication.

Retroviruses are used as vectors by replacing one or more of the endogenous trans-acting genes of a proviral form of the retrovirus with a recombinant therapeutic gene or, in the case of the present invention, a selectable fusion gene, and then transducing the recombinant provirus into a cell. The trans-acting genes include the gag, pol and env genes which encode, respectively, proteins of the viral core, the enzyme reverse transcriptase and constituents of the envelope protein, all of which are necessary for production of intact virions. Recombinant retroviruses deficient in the trans-acting gag, pol or env genes cannot synthesize essential proteins for replication and are accordingly replication-defective. Such replication-defective recombinant retroviruses are propagated using packaging cell lines. These packaging cell lines contain integrated retroviral genomes which provide all trans-acting gene sequences necessary for production of intact virions. Prioviral DNA sequences which are transduced into such packaging cell lines are transcribed into RNA and encapsidated into infectious virions containing the selectable fusion gene (and/or therapeutic gene), but, lacking the trans-acting gene products gag, pol and env, cannot synthesize the necessary gag, pol and env proteins for encapsidating the RNA into particles for infecting other cells. The resulting infectious retrovirus vectors can therefore infect other cells and integrate a selectable fusion gene into the cellular DNA of a host cell, but cannot replicate. Mann et al. (*Cell* 33:153, 1983), for example, describe the development of various packaging cell lines (e.g., Ψ2) which can be used to produce helper virus-free stocks of recombinant retrovirus. Encapsidation in a cell line harboring trans-acting elements encoding an ecotropic viral envelope (e.g., Ψ2) provides ecotropic (limited host range) progeny virus. Alternatively, assembly in a cell line containing amphotropic packaging genes (e.g., PA317, ATCC CRL 9078; Miller and Buttimore, *Mol. Cell. Biol.* 6:2895, 1986) provides amphotropic (broad host range) progeny virus.

Numerous provirus constructs have been used successfully to express foreign genes (see, e.g., Coffin, in Weiss et al. (eds.), *RNA Tumor Viruses*, 2nd Ed., Vol. 2, (Cold Spring Harbor Laboratory, New York, 1985, pp. 17–71). Most proviral elements are derived from murine retroviruses. Retroviruses adaptable for use in accordance with the present invention can, however, be derived from any avian or mammalian cell source. Suitable retroviruses must be capable of infecting cells which are to be the recipients of the new genetic material to be transduced using the retroviral vector. Examples of suitable retroviruses include avian retroviruses, such as avian erythroblastosis virus (AEV), avian leukosis virus (ALV), avian myeloblastosis virus (AMV), avian sarcoma virus (ASV), Fujinami sarcoma virus (FuSV), spleen necrosis virus (SNV), and Rous sarcoma virus (RSV); bovine leukemia virus (BLV); feline retroviruses, such as feline leukemia virus (FeLV) or feline sarcoma virus (FeSV); murine retroviruses, such as murine leukemia virus (MuLV); mouse mammary tumor virus (MMTV), and murine sarcoma virus (MSV); and primate retroviruses, such as human T-cell lymphotropic viruses 1 and 2 (HTLV-1, and -2), and simian sarcoma virus (SSV). Many other suitable retroviruses are known to those skilled in the art. A taxonomy of retroviruses is provided by Teich, in Weiss et al. (eds.), *RNA Tumor Viruses*, 2d ed., Vol. 2 (Cold Spring Harbor Laboratory, New York, 1985, pp. 1–160). Preferred retroviruses for use in connection with the present invention are the murine retroviruses known as Moloney murine leukemia virus (MoMLV), Moloney murine sarcoma virus (MoMSV), Harvey murine sarcoma virus (HaMSV) and Kirsten murine sarcoma virus (KiSV). The sequences required to construct a retroviral vector from the MoMSV genome can be obtained in conjunction with a pBR322 plasmid sequence such as pMV (ATCC 37190), while a cell line producer of KiSV in K-BALB cells has been deposited as ATCC CCL 163.3. A deposit of pRSVneo, derived from pBR322 including the RSV LTR and an intact neomycin drug resistance marker is available from ATCC under Accession No. 37198. Plasmid pPB101 comprising the SNV genome is available as ATCC 45012. The viral genomes of the above retroviruses are used to construct replication-defective retrovirus vectors which are capable of integrating their viral genomes into the chromosomal DNA of an infected host cell but which, once integrated, are incapable of replication to provide infectious virus, unless the cell in which it is introduced contains other proviral elements encoding functional active trans-acting viral proteins.

The selectable fusion genes of the present invention which are transduced by retroviruses are expressed by placing the selectable fusion gene under the transcriptional control of the enhancer and promoter incorporated into the retroviral LTR, or by placing them under the control of heterologous transcriptional control sequences inserted between the LTRs. Use of both heterologous transcriptional control sequences and the LTR transcriptional control sequences enables coexpression of a therapeutic gene and a selectable fusion gene in the vector, thus allowing selection of cells expressing specific vector sequences encoding the desired therapeutic gene product. Obtaining high-level expression may require placing the therapeutic gene and/or selectable fusion gene within the retrovirus under the transcriptional control of a strong heterologous enhancer and promoter expression cassette. Many different heterologous enhancers and promoters have been used to express genes in retroviral vectors. Such enhancers or promoters can be derived from viral or cellular sources, including mammalian genomes, and are preferably constitutive in nature. Such heterologous transcriptional control sequences are discussed above with reference to recombinant expression vectors. To be expressed in the transduced cell, DNA sequences introduced by any of the above gene transfer methods are usually expressed under the control of an RNA polymerase II promoter.

Particularly preferred recombinant expression vectors for use in mammalian cells include pLXSN, pLNCX and pLNL6, and derivatives thereof, which are described by Miller and Rosman, Biotechniques 7:980, 1989. These vectors are capable of expressing heterologous DNA under the transcriptional control of the retroviral LTR or the CMV promoter, and the neo gene under the control of the SV40 early region promoter or the retroviral LTR. For use in the present invention, the neo gene is replaced with the bifunctional selectable fusion genes disclosed herein, such as the HyTK (SEQ ID NO:1 selectable fusion gene or the CD-neo (SEQ ID NO:3 selectable fusion gene. Construction of useful replication-defective retroviruses is a matter of routine skill. The resulting recombinant retroviruses are capable of integration into the chromosomal DNA of an infected host cell, but once integrated, are incapable of replication to provide infectious virus, unless the cell in which it is introduced contains another proviral insert encoding functionally active trans-acting viral proteins.

Uses of Bifunctional Selectable Fusion Genes

The selectable fusion genes of the present invention are particularly preferred for use in gene therapy as a means for identifying, isolating or eliminating cells, such as somatic cells, into which the selectable fusion genes are introduced. In gene therapy, somatic cells are removed from a patient, transduced with a recombinant expression vector containing a therapeutic gene and the selectable fusion gene of the present invention, and then reintroduced back into the patient. Somatic cells which can be used as vehicles for gene therapy include hematopoietic (bone marrow-derived) cells, keratinocytes, hepatocytes, endothelial cells and fibroblasts (Friedman, *Science* 244:1275, 1989). Alternatively, gene therapy can be accomplished through the use of injectable vectors which transduce somatic cells in vivo. The feasibility of gene transfer in humans has been demonstrated (Kasid et al., *Proc. Natl. Acad. Sci. USA* 87:473, 1990; Rosenberg et al., *N. Engl. J. Med.* 323:570, 1990).

The selectable fusion genes of the present invention are particularly useful for eliminating genetically modified cells in vivo. In vivo elimination of cells expressing a negative selectable phenotype is particularly useful in gene therapy as a means for ablating a cell graft, thereby providing a means for reversing the gene therapy procedure. For example, it has been shown that administration of the anti-herpes virus drug ganciclovir to transgenic animals expressing the HSV-I TK gene from an immunoglobulin promoter results in the selective ablation of cells expressing the HSV-I TK gene (Heyman et al., *Proc. Natl. Acad. Sci. USA* 86:2698, 1989). Using the same transgenic mice, GCV has also been shown to induce full regression of Abelson leukemia virus-induced lymphomas (Moolten et al., *Human Gene Therapy* 1:125, 1990). In a third study, in which a murine sarcoma (K3T3) was infected with a retrovirus expressing HSV-I TK and transplanted into syngeneic mice, the tumors induced by the sarcoma cells were completely eradicated following treatment with GCV (Moolten and Wells, *J. Natl. Cancer Inst.* 82:297, 1990).

The selectable fusion genes of the present invention also are beneficial in tumor ablation therapy as it has been practiced by Oldfield et al., *Human Gene Therapy* 4:39, 1993. Packaging cells (about $10^6$–$10^9$) producing either the tgLS(+)HyTK or the tgLS(+)CDneo retroviral vectors are inoculated intra-tumorally. After a period of several days, during which the newly produced retroviruses infect the adjacent rapidly growing tumor cells, the patient is given about 2–20 mg of ganciclovir/kg body weight intravenously daily (when tgLS(+)HyTK retroviral vector has been used) or about 50–200 mg of 5-FC/kg orally daily (when tgLS(+)CDneo retroviral vector has been used) to selectively ablate the infected tumor cells.

The bifunctional selectable fusion genes of the present invention can also be used to facilitate gene modification by homologous recombination. Reid et al., *Proc. Natl. Acad. Sci. USA* 87:4299, 1990 has recently described a two-step procedure for gene modification by homologous recombination in ES cells ("in-out" homologous recombination) using the HPRT gene. Briefly, this procedure involves two steps: an "in" step in which the HPRT gene is embedded in target gene sequences, transfected into HPRT⁻ host cells and homologous recombinants having incorporated the HPRT gene into the target locus are identified by their growth in HAT medium and genomic analysis using PCR. In a second "out" step, a construct containing the desired replacement sequences embedded in the target gene sequences (but without the HPRT gene) is transfected into the cells and homologous recombinants having the replacement sequences (but not the HPRT gene) are isolated by negative selection against HPRT⁺ cells. Although this procedure allows the introduction of subtle mutations into a target gene without introducing selectable gene sequences into the target gene, it requires positive selection of transformants in a HPRT⁻ cell line, since the HPRT gene is recessive for positive selection. Also, due to the inefficient expression of the HPRT gene in ES cells, it is necessary to use a large 9-kbp HPRT mini-gene which complicates the construction and propagation of homologous recombination vectors. The selectable fusion genes of the present invention provide an improved means whereby "in-out" homologous recombination may be performed. Because the selectable fusion genes of the present invention are dominant for positive selection, any wild-type cell may be used (i.e., one is not limited to use of cells deficient in the selectable phenotype). Moreover, the size of the vector containing the selectable fusion gene is reduced significantly relative to the large HPRT mini-gene.

By way of illustration, the HyTK (SEQ ID NO:1 selectable fusion gene is used as follows: In the first "in" step, the HyTK (SEQ ID NO:1 selectable fusion gene is embedded in target gene sequences, transfected into a host cell, and homologous recombinants having incorporated the HyTK (SEQ ID NO:1 selectable fusion gene into the target locus are identified by their growth in medium containing Hm followed by genome analysis using PCR. The HyTK⁺ cells are then used in the second "out" step, in which a construct containing the desired replacement sequences embedded in the target gene sequences (but without the HyTK (SEQ ID NO:1 selectable fusion gene) is transfected into the cells. Homologous recombinants are isolated by selective elimination of HyTK⁺ cells using ganciclovir followed by genome analysis using PCR.

EXAMPLES

Example 1

Construction and Characterization of Plasmid Vectors Containing HyTK (SEQ ID NO:1 Selectable Fusion Gene A. Construction of the Bifunctional HyTK (SEQ ID NO:1 Selectable Fusion Gene. The hph and HSV-I TK genes were first placed under the regulatory control of the HCMV promoter in tgCMV/hygro and tgCMV/TK, respectively. Plasmid tgCMV/hygro (FIG. 1) consists of the following elements: the BalI-SstII fragment containing the HCMV IE94 promoter (Boshart et al., *Cell* 41:521, 1985); an oligonucleotide containing a sequence conforming to a consensus translation initiation sequence of mammalian cells (GCCGCCACC ATG) (SEQ ID NO:5) (Kozak, *Nucl. Acid Res.* 15:8125, 1987); nucleotides 234–1256 from the hph gene (Kaster et al., *Nucl. Acids. Res.* 11:6895, 1983), encoding hygromycin phosphotransferase; the BclI-BamHI fragment from the SV40 genome (Tooze, J., ed., *Molecular Biology of Tumor Viruses*, 2nd Ed. DNA Tumor Viruses, Cold Spring Harbor Laboratory, New York, 1981), containing the SV40 early region polyadenylation sequence; the NruI-AlwNI fragment from pML2d (Lusky and Botchan, *Nature* 293:79, 1981), containing the bacterial replication origin; and the AlwNI-AatII fragment from pGEM1 (Promega Corporation), containing the β-lactamase gene.

Plasmid tgCMV/TK (FIG. 1) is similar to tgCMV/hygro, but contains nucleotides 519–1646 from the HSV-I TK gene (Wagner et al., *Proc. Natl. Acad. Sci USA* 78:1441, 1981) in place of the hph gene.

Plasmid tgCMV/HyTK (FIG. 1), containing the selectable fusion gene comprising the hph gene fused to the HSV-I TK gene, was constructed by inserting the 1644-bp SpeI-ScaI fragment from tgCMV/hygro between the SpeI and MluI sites of tgCMV/TK. Before ligation, the MluI site in the HSV-I TK gene was treated with T4 DNA polymerase to allow blunt end ligation with the ScaI site, thus preserving the open reading frame. Translation of this fused gene (referred to as the HyTK (SEQ ID NO:1 and (SEQ ID NO:2) selectable fusion gene) was expected to generate a single bifunctional fusion protein, consisting of amino acids 1–324 from the hph protein and amino acids 10–376 from the HSV-I TK protein. The C-terminal 17 amino acids of the hph protein, and the N-terminal 9 amino acids of the TK protein, were deleted in the bifunctional fusion protein.

B. Dominant Positive Selection of Cells Containing the HyTK (SEQ ID NO:1 Selectable Fusion Gene. To demonstrate that the HyTK (SEQ ID NO:1 selectable fusion gene encodes both hph and TK enzymatic activities, the frequencies with which tgCMV/HyTK conferred hygromycin resistance ($Hm^r$) (in NIH/3T3 cells and Rat-2 cells), and the ability to grow in medium containing hypoxanthine, aminopterin, and thymidine ($HAT^r$) (in Rat-2 cells) were compared with those of the parental plasmids, tgCMV/hygro and tgCMV/TK, respectively.

NIH/3T3 cells were grown in Dulbecco's Modified Eagle Medium (DMEM; Gibco Laboratories) supplemented with 10% bovine calf serum (Hyclone), 2 mM L-glutamine, 50 U/ml penicillin, and 50 µg/ml streptomycin at 37° C. in a humidified atmosphere supplemented with 10% $CO_2$. $TK^-$ Rat-2 cells (Topp, *Virology* 113:408, 1981) were grown in DMEM supplemented with 10% fetal bovine serum (Hyclone), 2 mM L-glutamine, 50 U/ml penicillin, and 50 µg/ml streptomycin at 37° C. in a humidified atmosphere supplemented with 10% $CO_2$. NIH/3T3 and Rat-2 cells were transfected with the DNA vectors described above by electroporation, as follows. Exponentially growing NIH/3T3 and Rat-2 cells were harvested by trypsinization, washed free of serum, and resuspended in DMEM at a concentration of $10^7$ cells/ml. Supercoiled plasmid DNA (5 µg) was added to 800 µl of cell suspension ($8 \times 10^6$ cells), and the mixture subjected to electroporation using the Biorad Gene Pulser and Capacitance Extender (200–300 V, 960 µF., 0.4 cm electrode gap, at ambient temperature). Following transfection, the cells were returned to 9-cm dishes and grown in non-selective medium. After 24 hours, the cells were trypsinized, seeded at $6 \times 10^5$ per 9-cm dish, and allowed to attach overnight. The non-selective medium was replaced with selective medium (containing 500 µg/ml hygromycin B for NIH/3T3 cells, and 300 µg/ml hygromycin B or HAT for Rat-2 cells), and selection was continued for approximately 10–12 days until colonies were evident. The plates were stained with methylene blue and counted. The results are shown in Table 1 below. The number of colonies reported is the average number of colonies per 9-cm dish.

TABLE 1

Positive Selection Using HyTKa30 Fusion Gene

| | NIH/3T3 Cells | Rat-2 Cells | |
| --- | --- | --- | --- |
| Plasmid | No. $Hm^r$ Colonies | No. $Hm^r$ Colonies | No. $HAT^r$ Colonies |
| tgCMV/hygro | 45 | 368 | nt |
| tgCMV/TK | nt | nt | 356 |
| tgCMV/HyTK | 100 | 428 | 124 |

In both cell lines, tgCMV/HyTK gave rise to $Hm^r$ colonies at a slightly higher frequency than tgCMV/hygro. However, in Rat-2 cells, tgCMV/HyTK was slightly less efficient than tgCMV/TK in generating $HAT^r$ colonies. This demonstrates that the HyTK (SEQ ID NO:1 selectable fusion gene encodes both hph and TK enzymatic activities, although with altered efficiencies.

C. Negative Selection of Cells Containing the HyTK (SEQ ID NO:1 Selectable Fusion Gene. To investigate the utility of the HyTK (SEQ ID NO:1 selectable fusion gene for negative selection, the colonies resulting from each transfection (Table 1) were pooled and expanded into cell lines for further analysis. The $Hm^r$ NIH/3T3 cell pools and the $Hm^r$ and $HAT^r$ Rat-2 cell pools were tested for $GCV^s$ in a short term cell proliferation assay as follows.

The transfected NIH/3T3 and Rat-2 cells ($3 \times 10^4$ of each) were seeded into 9-cm tissue culture dishes in complete growth medium, and allowed to attach for 4 hours. The medium was then supplemented with various concentrations of GCV (Syntex, Palo Alto, Calif.), and the cells incubated for an additional 60 hours. At this time, the medium was removed, the attached cells were harvested by trypsinization and stained with trypan blue, and the viable cells were counted. Cell growth was expressed as a fraction of the cell growth observed in the absence of GCV. The results shown are the average of triplicate assays.

Figure 3:
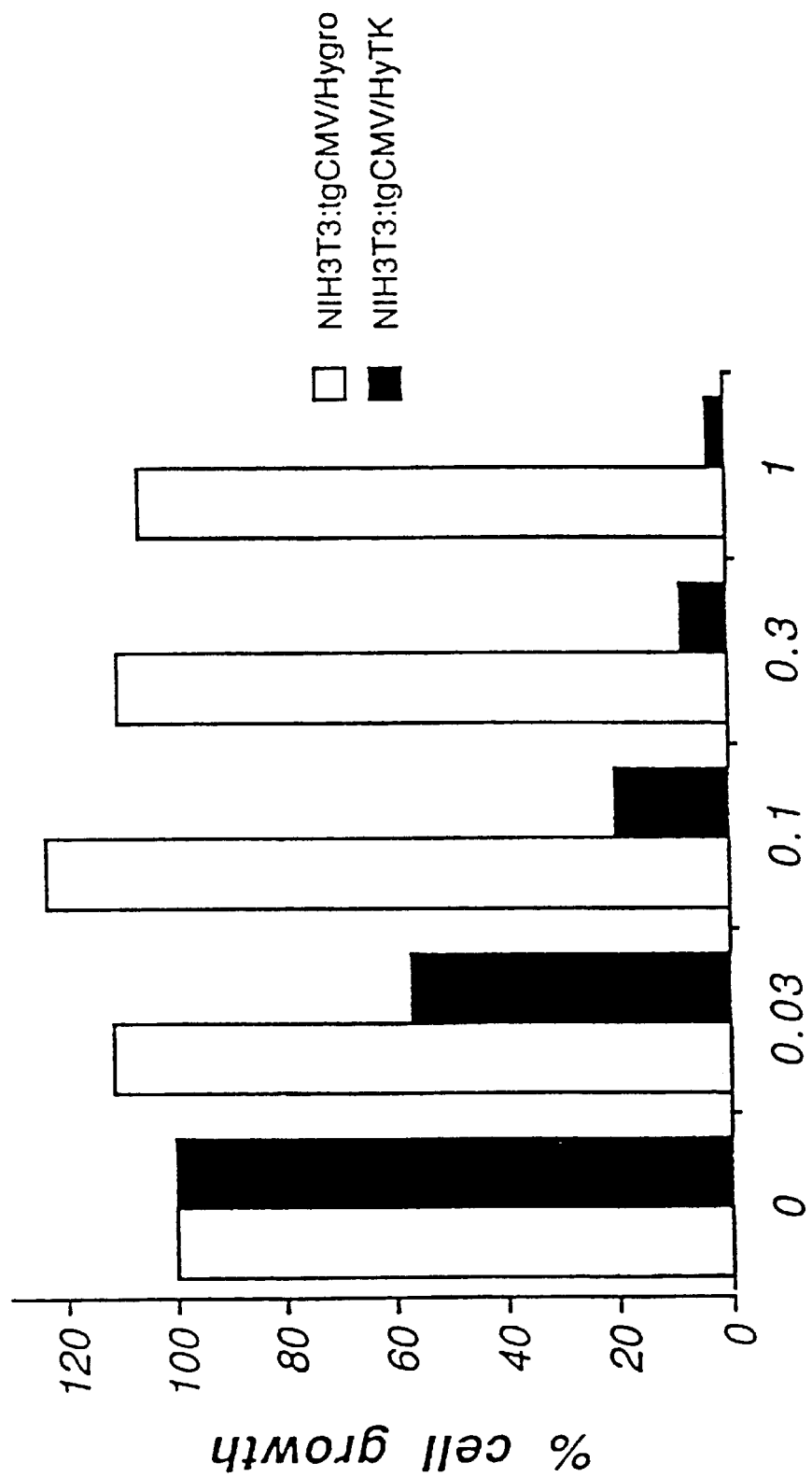
FIGS. 3 and 4 are graphs showing the results of a short-term proliferation assay in which the hygromycin resistant ($Hm^r$) NIH/3T3 cell pools and $Hm^r$ and HAT resistant ($HAT^r$) Rat-2 cell pools were tested for ganciclovir sensitivity ($GCV^s$).

The result shown in FIG. 3 demonstrates that the HyTKt (SEQ ID NO:1 selectable fusion gene conferred $GCV^s$ in NIH/3T3 cells. The degree of inhibition of cell growth was proportional to the concentration of GCV used, and approached 100% at a concentration of 1 µM. In contrast, NIH/3T3 cells transfected with tgCMV/hygro were not adversely affected by GCV over the range of concentrations tested (0.03 µM–1.0 µM).

Figure 4:
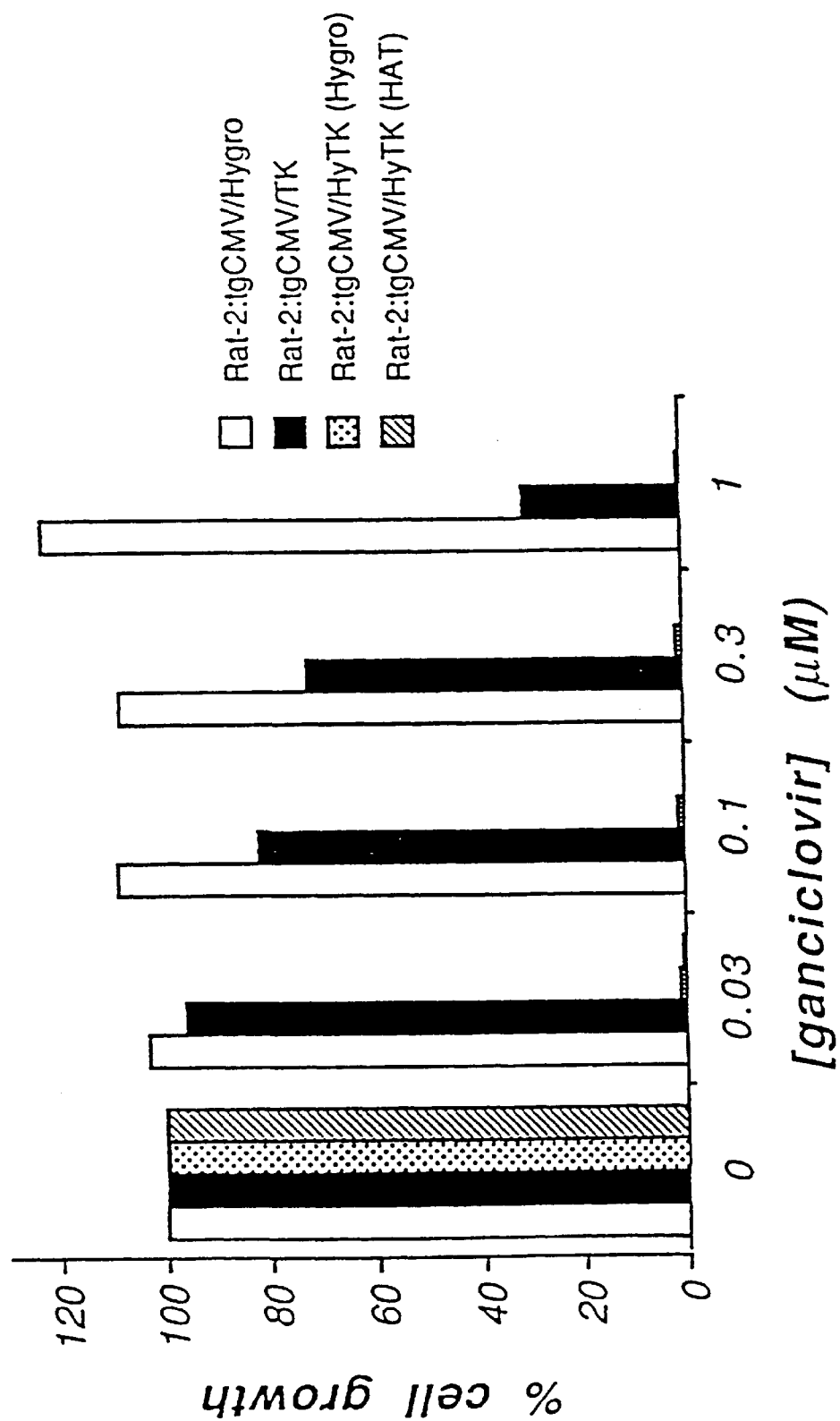

The results shown in FIG. 4 indicate that the HyTK (SEQ ID NO:1 selectable fusion gene was more effective than the HSV-I TK gene for negative selection in Rat-2 cells. Growth of Rat-2 cells transfected with tgCMV/HyTK was almost completely inhibited even at the lowest concentration of GCV used (0.03 µM), whether the cells were initially selected for $Hm^r$ or $HAT^r$. Growth of Rat-2 cells transfected with tgCMV/hygro was not inhibited by GCV over the range of concentrations tested (0.03 µM 1.0 µM). The growth of Rat-2 cells transfected with tgCMV/TK was inhibited by GCV, but the concentrations required for growth inhibition were much higher than those required to inhibit the growth of Rat-2 cells transfected with tgCMV/HyTK. The Rat-2 cells transfected with tgCMV/TK were less sensitive to GCV than the Rat-2 cells transfected with tgCMV/HyTK. This appears to conflict with the result obtained when the two genes were used for positive selection in Rat-2 cells (Table 1), which indicated that the HyTK (SEQ ID NO:1 selectable fusion gene was less effective than the HSV-I TK gene in conferring $HAT^r$; A further observation concerning the relative sensitivities of these cell lines to GCV was that the NIH/3T3 cells transfected with tgCMV/HyTK were less sensitive to GCV than the Rat-2 cells transfected with tgCMV/HyTK.

D. Northern Analysis of Transfected Cell Lines. To investigate the basis for the differential sensitivities of the $Hm^r$ and $HAT^r$ NIH/3T3 and Rat-2 cell pools to GCV (FIGS. 3 and 4), and the altered efficiency, with which the HyTK (SEQ ID NO:1 selectable fusion gene gave rise to $Hm^r$ and $HAT^r$ colonies (Table 1), Northern blots of mRNA from each cell pool were probed with sequences from the hph and HSV-I TK genes, as follows.

Polyadenylated mRNA was prepared according to standard procedures (Ausabel et al., Eds., *Current Protocols in Molecular Biology*, Wiley, New York, 1987). RNA samples (10 µg) were electrophoresed through 1.1% agarose gels containing formaldehyde as described (Ausabel et al., supra). Following electrophoresis, the gels were inverted and blotted by capillary transfer in 20×SSC onto Duralon UV nylon membranes (Stratagene). After fixing the mRNA to the membrane by UV-irradiation (0.12 J/$cm^2$), the membranes were incubated in Stark's buffer (50% formamide, 5×SSC, 50 mM potassium phosphate (pH 6.5), 1% SDS, 0.1% Ficoll, 0.1% PVP, 0.1% BSA, 300 µg/ml sheared and denatured salmon sperm DNA, 0.05% Sarkosyl) at 50° C. for several hours. A uniformly labeled single stranded antisense RNA probe specific for hph was prepared (Ausabel et al., supra), 1×10$^6$ cpm/ml were added to the hybridization mixture, and the incubation was continued at 63° C. for 15 h. The membrane was then washed in 0.1×SSC, 0.1% SDS at 63° C., and exposed to autoradiographic film (Kodak XAR-5). For detection of HSV-I TK and β-actin sequences, gel-purified restriction fragments from the HSV-I TK and β-actin genes were radiolabeled by random priming (Ausabel et al., supra). Membranes were pre-hybridized in Stark's buffer at 42° C. for 15 hours. The membranes were then washed in 6×SSC, 1% SDS at 63° C., and exposed to autoradiographic film (Kodak XAR-5).

Figure 5:
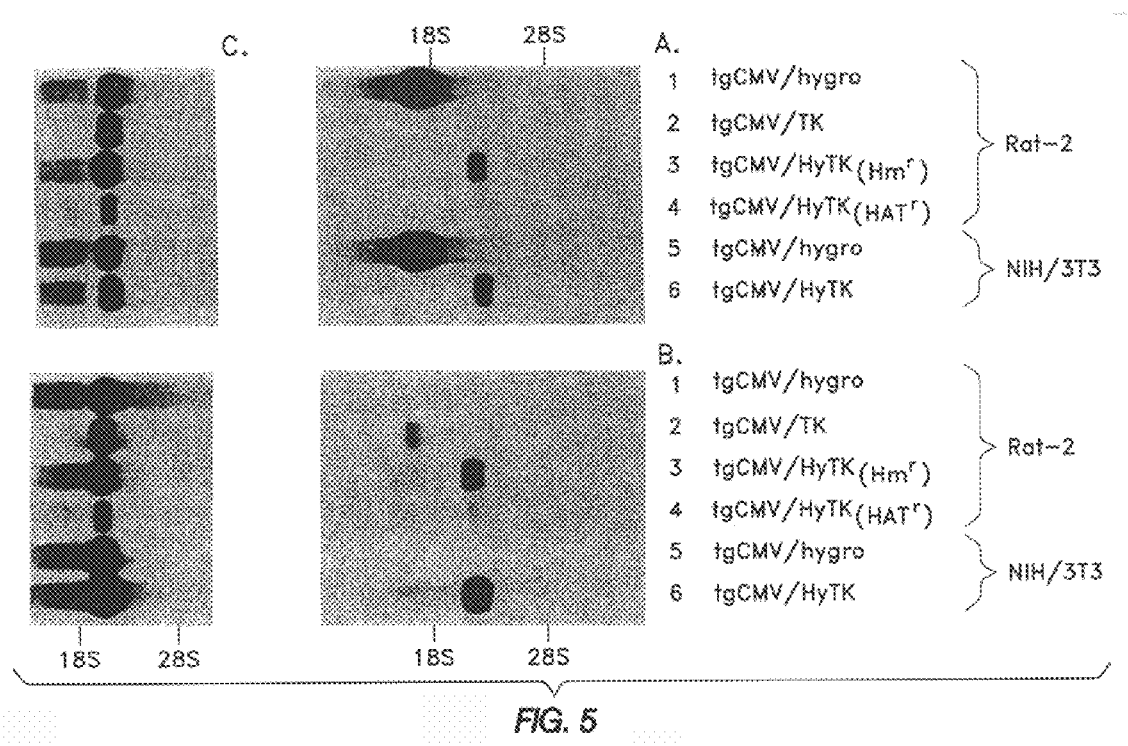
FIGS. 5A–5C show the results of Northern analysis of $Hm^r$ and $HAT^r$ cell pools. Polyadenylated mRNA was extracted from each $Hm^r$ and $HAT^r$ cell pool, and used to prepare Northern blots which were probed with sequences from the hph gene (Panel A), the HSV-I TK gene (Panel B), or the β-actin gene (Panel C) (for mRNA equivalence). The positions of the 28S and 18S ribosomal RNAs are indicated. The mRNA present in each lane was extracted from the following cells: Lane 1, Rat-2 cells transfected with tgCMV/hygro; Lane 2, Rat-2 cells transfected with tgCMV/TK; Lane 3, Rat-2 cells transfected with tgCMV/HyTK and selected for $Hm^r$; Lane 4, Rat-2 cells transfected with tgCMV/HyTK and selected for $HAT^r$; Lane 5, NIH/3T3 cells transfected with tgCMV/hygro; Lane 6, NIH/3T3 cells transfected with tgCMV/HyTK.

In both Rat-2 and NIH/3T3 cells, the steady state level of mRNA detected with the hph probe was higher in the cells transfected with tgCMV/hygro than the cells transfected with tgCMV/HyTK and selected from Hm$^r$ (FIG. 5, gel A, lanes 5 and 6). This may indicate that a higher level of expression of the hph gene is required to confer resistance to equivalent levels of hygromycin B (300 µg/ml in Rat-2, and 500 µg/ml in NIH/3T3), due to the fact that the bifunctional fusion protein is more effective than the hph protein at inactivating hygromycin B, or is more stable than the hph protein. This conclusion is supported by the results in Table 1, which show that tgCMV/HyTK gave rise to a slightly greater number of Hm$^r$ colonies in both cell lines than did tgCMV/hygro.

The RNA Northern analysis also indicated that the Rat-2 cells transfected with tgCMV/TK expressed a steady state level of mRNA similar to the Rat-2 cells transfected with tgCMV/HyTK and selected for HAT$^r$ (FIG. 5, gel B, lanes 2 and 4). However, tgCMV/TK gave rise to a greater number of HAT$^r$ cells than did tgCMV/HyTK (Table 1). This suggests that the HyTK (SEQ ID NO:1 selectable fusion protein is less effective than the HSV-I TK protein at phosphorylating thymidine, or is less stable than the HSV-I TK protein.

Finally, the Rat-2 cells transfected with tgCMV/HyTK expressed steady state levels of mRNA several fold higher than (when selected for Hm$^r$; FIG. 5, gel B, lane 3), or similar to (when selected for HAT$^r$; FIG. 5, gel b, lane 4), the Rat-2 cells transfected with tgCMV/TK (FIG. 5, gel B. lane 2). However, both the Rat-2 cell pools transfected with tgCMV/HyTK were over 30-fold more sensitive to GCV than the Rat-2 cells transfected with tgCMV/TK (FIG. 4). This suggests that the bifunctional fusion protein is markedly more effective than the HSV-I TK protein at phosphorylating ganciclovir, or is markedly more stable than the HSV-I TK protein. The increased ability of the bifunctional fusion protein to confer GCV$^s$, and the concomitant decreased ability to confer HAT$^r$, suggests that the substrate affinity of the bifunctional fusion protein is altered relative to that of the HSV-I TK protein, rather than the stability.

Example 2

Construction and Characterization of Retroviral Vectors Containing HyTK (SEQ ID NO:1 Selectable Fusion Gene A. Construction of Retroviral Vectors. Two retroviral expression vectors containing the HyTK (SEQ ID NO:1 selectable fusion gene were constructed. In the first, tgLS (+)HyTK (SEQ ID NO:1 the HyTK (SEQ ID NO:1 selectable fusion gene was placed under the regulatory control of the promoter present in the retroviral LTR. In the second, tgLS(−)CMV/HyTK, the HyTK (SEQ ID NO:1 selectable fusion gene was placed under the regulatory control of the HCMV promoter.

Figure 2:
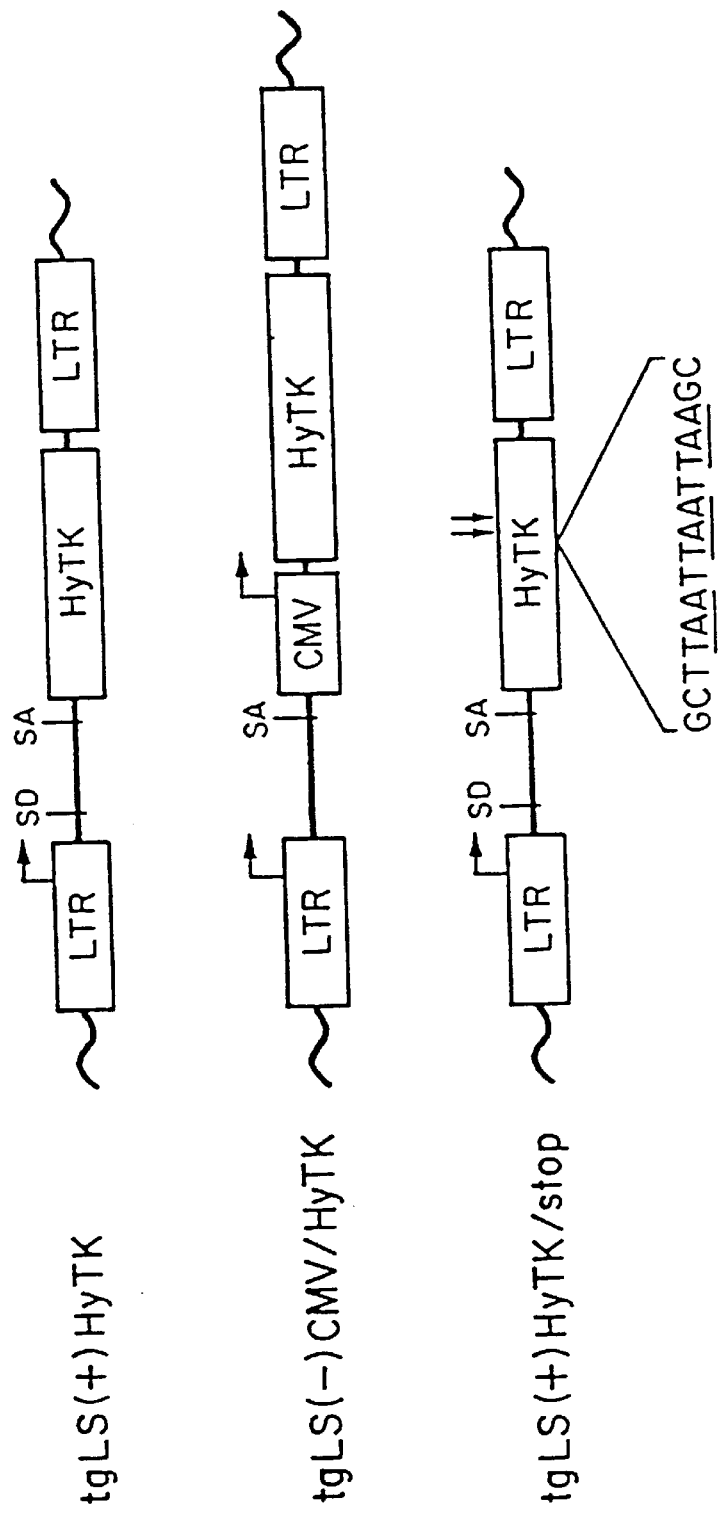
FIG. 2 shows diagrams of the proviral structures of the retroviral vectors tgLS(+)HyTK, tgLS(−)CMV/HyTK and tgLS(+)HyTK/stop used in the present invention. The horizontal arrows indicate transcriptional start sites and direction of transcription. The open box labeled LTR is the retroviral long terminal repeat. The viral splice donor is labeled SD and the acceptor sequences are labeled SA. The open box labeled CMV is the cytomegalovirus promoter. In tgLS(+)HyTK/stop, the positions of the two internal initiation codons retained in the HyTK (SEQ ID NO:1 selectable fusion gene are indicated by vertical arrows. The location at which the universal translation terminator oligonucleotide was inserted is also marked.

The retroviral expression vector tgLS(+)HyTK (the proviral structure of which is shown in FIG. 2) consists of the following elements: the 5' LTR and sequences through the PstI site at nucleotide 984 of MoMSV (Van Beveren et al., Cell 27:97, 1981); sequenced from the PstI site at nucleotide 563 to nucleotide 1040 of MoMLV (Shinnick et al., Nature 293:543, 1981), incorporating point mutations (ATG→TAG) which eliminate the Pr65 gag translation initiation codon (Bender et al., J. Virol. 61:1639, 1987); a fragment from tgCMV/HyTK, containing the HyTK selectable fusion gene; sequences from nucleotide 7764 and through the 3' LTR of MoMLV (Shinnick et al., Nature 293:543, 1981); the NruI-AlwNI fragment from pML2d (Lusky and Botchan, Nature 293:79, 1981), containing the bacterial replication origin; and the AlwNI-AatII fragment from pGEM1 (Promega Corporation), containing the β-lactamase gene.

The retroviral expression vector tgLS(−)CMV/HyTK (the proviral structure of which is shown in FIG. 2) is similar to tgLS(+)HyTK, but carries a point mutation (AGGT→AGGC) which eliminates the MoMSV-derived splice donor sequence (transferred from the retroviral vector, ΔH [Overell et al., Mol. Cell. Biol. 8:1803, 1988]); and contains the HCMV promoter upstream of the HyTK (SEQ ID NO:1 selectable fusion gene sequences.

The retroviral expression vector tgLS(+)HyTK/stop (the proviral structure of which is shown in FIG. 2) was derived from tgLS(+)HyTK by inserting the universal translation terminator oligonucleotide (Pharmacia), 5'-GCTTAATTAATTAAGC-3' (SEQ ID NO:6), at the NaeI site located near the junction of the hph and HSV-I TK sequences of the HyTK (SEQ ID NO:1 selectable fusion gene.

B. Generation of Stable Cell Lines Producing Retroviral Vectors. Stable Ψ2 packaging cell lines were generated which produce the above ecotropic retroviruses as follows. Ψ2 cells (Mann et al., Cell 33:153, 1983) were grown in Dulbecco's Modified Eagle Medium (DMEM; Gibco Laboratories) supplemented with 10% bovine calf serum (Hyclone), 2 mM L-glutamine, 50 U/ml penicillin, and 50 µg/ml streptomycin at 37° C. in a humidified atmosphere supplemented with 10% $CO_2$. PA317 cells (Miller and Buttimore, Mol. Cell. Biol. 6:2895, 1986) were grown in DMEM supplemented with 10% fetal bovine serum (Hyclone), 2 mM L-glutamine, 50 U/ml penicillin, and 50 µg/ml streptomycin at 37° C. in a humidified atmosphere supplemented with 10% $CO_2$.

The retroviral expression vectors described above were first transfected into PA317 amphotropic packaging cells by electroporation. Amphotropic virions produced by the transiently transfected PA317 packaging cells were then used to infect the Ψ2 cells as follows. Exponentially growing PA317 cells were harvested by trypsinization, washed free of serum, and resuspended in DMEM in a concentration of 10$^7$ cells/ml. Supercoiled plasmid DNA (5 µg) was added to 800 µl of cell suspension (8×10$^6$ cells) and the mixture subjected to electroporation using the Biorad Gene Pulser and Capacitance Extender (200–300 V, 960 µF, 0.4 cm electrode gap, at ambient temperature). The transfected PA317 cells were then transferred to a 9-cm tissue culture dish containing 10 ml of complete growth medium supplemented with 10 mM sodium butyrate (Sigma Chemical Co.), and allowed to attach overnight. After 15 hours, the medium was removed and replaced with fresh medium. After a further 24 hours, the medium containing transiently produced amphotropic retrovirus particles was harvested, centrifuged at 2000 rpm for 10 min, and used to infect the Ψ2 ecotropic packaging cells. Exponentially dividing Ψ2 cells were plated at a density of $10^6$ cells per 9-cm tissue culture dish, and allowed to attach overnight. The following day, the medium was removed and replaced with serial dilutions of the virus-containing supernatant (6 ml/dish) in medium supplemented with 4 μg/ml Polybrene hexadimethrine bromide (Sigma Chemical Co.). Infection of the Ψ2 cells by the viral particles was allowed to proceed overnight, and then the supernatant was replaced with complete growth medium. Infected cells were selected for drug resistance after a further 8–24 hours of growth by adding hygromycin B (Calbiochem) to a final concentration of 500 μg/ml. Colonies of $Hm^r$ cells were isolated using cloning cylinders 12–14 days later, and individually expanded into bulk cultures for analysis. Southern analysis (data not shown) revealed that the proviral structures were intact in six out of six independent clones, indicating that the HyTK (SEQ ID NO:1 selectable fusion gene is compatible with the retroviral life cycle.

C. Transduction of $Hm^r$, $HAT^r$, and $GCV^s$ by taLS(+)HyTK and tgLS(−)CMV/HyTK Retroviral Expression Vectors. The infected Ψ2 clones were titered on NIH/3T3 cells (selecting for $Hm^r$), and on Rat-2 cells (selecting for $Hm^r$, or for $HAT^r$) (Table 2), as follows. The Ψ2 clones producing the virus were grown to confluence in 9-cm tissue culture dishes, then fed with 15 ml of drug-free medium. After an overnight incubation, aliquots of supernatant were taken for assay. Exponentially dividing NIH/3T3 or Rat-2 cells were harvested by trypsinization and seeded at a density of $2.5 \times 10^4$ cells per 35-mm well in 6-well tissue culture trays. The following day, the medium was replaced with serial dilutions of virus-containing supernatant (1 ml/well) in medium supplemented with 4 μg/ml Polybrene hexadimethrine bromide (Sigma Chemical Co.). All supernatants were centrifuged at 2000 rpm for 10 min before use to remove viable cells. Infection was allowed to proceed overnight, and then the supernatant was replaced with complete growth medium. Infected cells were selected for drug resistance after a further 8–24 hours of growth by adding hygromycin B (Calbiochem) to a final concentration of 500 μg/ml (NIH/3T3 cells) or 300 μg/ml (Rat-2 cells), or by adding HAT supplement (Gibco) (Rat-2 cells). After a total of 12–14 days of growth, cells were fixed in situ with 100% methanol, and stained with methylene blue.

As shown in Table 2, below, both retroviruses conferred $Hm^r$ (to NIH/3T3 and Rat-2 cells) and $HAT^r$ (to Rat-2 cells). All viruses were harvested from a clone of infected Ψ2 cells.

TABLE 2

Titers of Ecotropic Retroviruses Produced by Ψ2 Packaging Cells on NIH/3T3 Cells and Rat-2 Cells

| Virus | NIH/3T3 $Hm^r$ CFU/ml | Rat-2 $Hm^r$ CFU/ml | Rat-2 $HAT^r$ CFU/ml |
|---|---|---|---|
| tgLS(+)HyTK (clone 5.5) | $1.8 \times 10^7$ | $1.6 \times 10^7$ | $4 \times 10^6$ |
| tgLS(−)CMV/HyTK (clone 6.2) | $1 \times 10^6$ | $1 \times 10^6$ | $8 \times 10^5$ |

To demonstrate that the tgLS(+)HyTK and tgLS(−)CMV/HyTK retroviruses. also conferred $GCV^s$, NIH/3T3 cells infected with the two retroviruses were selected for $Hm^r$ (500 μg/ml) for 10 days, and then pooled, expanded, and tested for $GCV^s$ in the following long-term cell proliferation assay.

Figure 6:
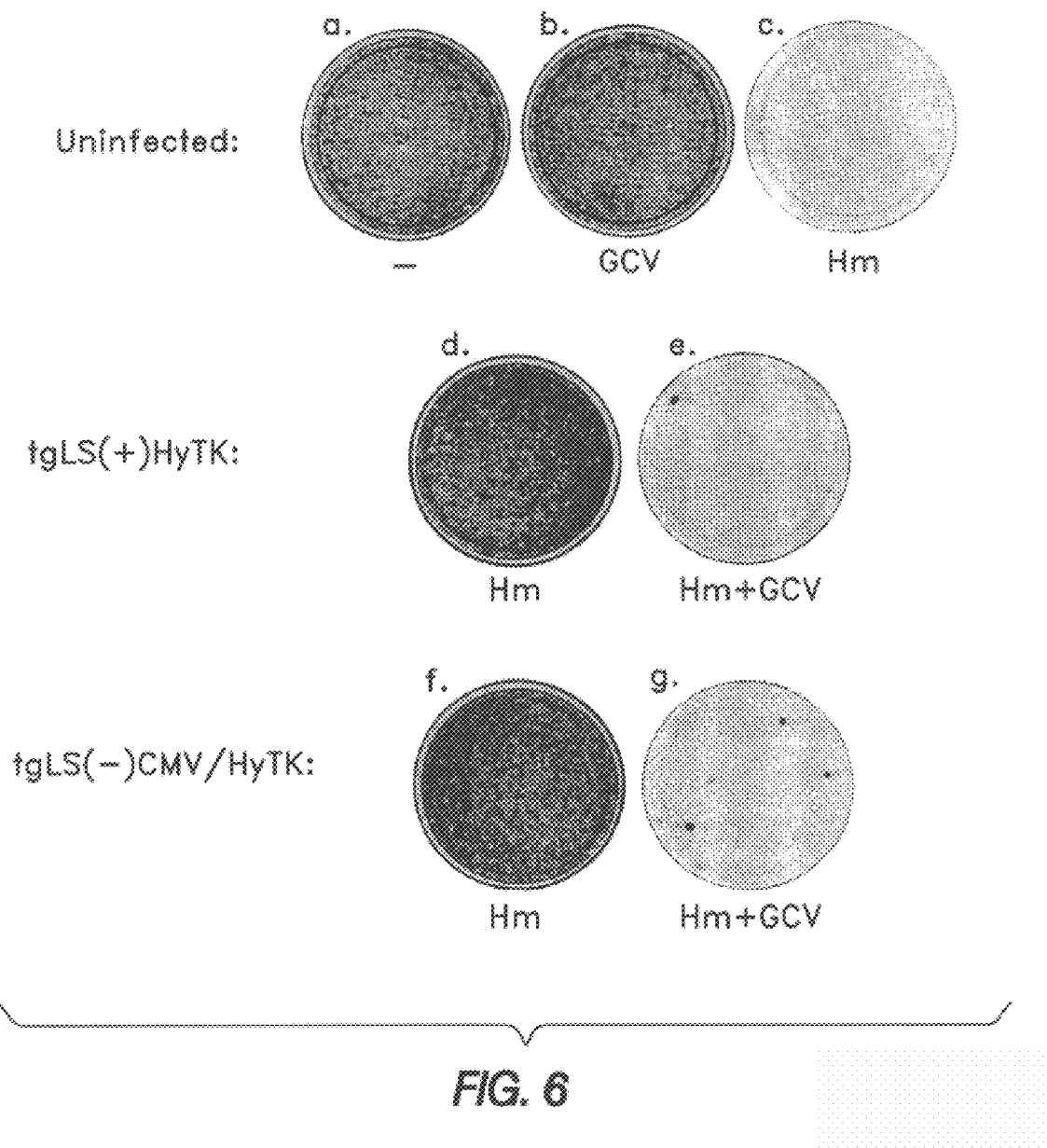
FIGS. 6a–g show photographs of stained colonies of uninfected NIH/3T3 cells (plates a, b and c) and NIH/3T3 cells infected with the tgLS(+)HyTK (plates d and e) or tgLS(−)CMV/HyTK (plates f and g) retroviruses. The cells were grown in medium alone or medium supplemented with GCV, Hm or Hm plus GCV in a long-term proliferation assay. The data show that uninfected NIH/3T3 cells were resistant to GCV and grew to confluence (plate b), but were killed by Hm (plate c). Growth of NIH/3T3 cells infected with the tgLS(+)HyTK and tgLS(−)CMV/HyTK retroviruses and grown in the presence of Hm (plates d and f) was inhibited by GCV (plates e and g).

Uninfected NIH/3T3 cells and the infected NIH/3T3 cell pools were plated at relatively low cell density ($10^4$ cells/9-mm dish) in complete growth medium and allowed to attach for 4 hours. The medium was then supplemented with hygromycin B (500 μg/ml), with or without 1 μM GCV, and the cells incubated for a period of 10 days. The medium was then removed and the cells were fixed in situ with 100% methanol and stained with methylene blue. The growth of both cell pools, as measured by colony formation, was almost completely inhibited by GCV (FIG. 6, plates e and g), indicating that both retroviruses conferred $Hm^r$ and $GCV^s$. Uninfected NIH/3T3 were resistant to this concentration of GCV, and grew to a confluent monolayer (FIG. 6, plate b), but were completely killed by 500 μg/ml Hm (FIG. 6, plate c). Colonies of cells resistant to both Hm and GCV were obtained at a low frequency ($10^{-4}$–$10^{-3}$) from the retrovirus-infected populations (FIG. 6, plates e and g). The proviruses present in the cells that gave rise to these colonies had likely suffered point mutations, or very small deletions or rearrangements in the HSV-I TK moiety which eliminated the ability to phosphorylate GCV. Similar results were also obtained with Rat-2 cell lines infected with tgLS(+)HyTK or with tgLS(−)CMV/HyTK (data not shown).

Example 3

Evidence for the Production of Bifunctional Selectable Fusion Protein

In HSV-I infected cells, the HSV-I TK gene normally utilizes three translation initiation sites, and encodes three nested polypeptides which all possess TK activity (Haarr et al., *J. Virol.* 56:512, 1985). Since the HyTK (SEQ ID NO:1 selectable fusion gene retains two of these initiation codons, it was conceivable that, as a result of translation initiation at one or both of these internal AUG codons, the HyTK (SEQ ID NO:1 selectable fusion gene might also encode nested polypeptides possessing TK activity. The bifunctional fusion protein, while retaining hph activity, might or might not possess TK activity. To rule out this possibility, an oligonucleotide sequence, 5'-GCTTAATTAATTAAGC-3'(SEQ ID NO:6), bearing translation termination codons in all three reading frames, was introduced into the HyTK (SEQ ID NO:1 selectable fusion gene in tgLS(+)HyTK, generating the construct designated tgLS(+)HyTK/stop (FIG. 1B). The oligonucleotide was inserted at a NaeI site downstream of the hph-derived sequences, but upstream of the two internal AUG codons in the HSV-I TK-derived sequences of the HyTK (SEQ ID NO:1 selectable fusion gene (FIG. 1B). The tgLS(+)HyTK and the tgLS(+)HyTK/stop retroviral expression vectors were transfected into Ψ2 cells, and the transiently produced virus was used to infect Rat-2 cells, which were then selected for $Hm^r$ or $HAT^r$ (Table 3). The retroviral expression vector tgLS(+)HyTK transduced both $Hm^r$ and $HAT^r$, but retroviral expression vector tgLS(+)HyTK/stop was only able to transduce $Hm^r$. Insertion of the translation termination codons completely abolished the ability of the retrovirus to transduce $HAT^r$, indicating that the internal translation initiation codons were not utilized in the HyTK (SEQ ID NO:1 selectable fusion gene, and the HyTK (SEQ ID NO:1 selectable fusion gene does indeed encode a bifunctional fusion protein. Viruses were harvested from transiently transfected Ψ2 cells.

TABLE 3

Titers of Ecotropic Retroviruses Produced Transiently
in Ψ2 Packaging Cells on NIH/3T3 and Rat-2 Cells

| Virus | NIH/3T3 Hm$^r$ CFU/ml | Rat-2 Hm$^r$ CFU/ml | Rat-2 HAT$^r$ CFU/ml |
|---|---|---|---|
| tgLS(+)HyTK | $4.5 \times 10^4$ | $9.5 \times 10^3$ | $1.1 \times 10^4$ |
| tgLS(−)CMV/HyTK | $2.6 \times 10^4$ | $5.9 \times 10^4$ | 0 |

As described in the above examples, retroviral expression vectors containing the HyTK (SEQ ID NO:1 selectable fusion gene were constructed and used to demonstrate the efficacy of the HyTK selectable fusion gene for positive and negative selection in NIH/3T3 and Rat-2 cells. High titer virus stocks were generated, which conferred both Hm$^r$ and HAT$^r$ on infected cells. Infected cells contained unrearranged proviruses and were killed (>99.9%) by GCV. The HyTK (SEQ ID NO:1 selectable fusion gene was slightly more effective than the hph gene at conferring Hm$^r$ in both NIH/3T3 and Rat-2 cells (Table 1). Genetic evidence that the HyTK (SEQ ID NO:1 selectable fusion gene encodes a bifunctional fusion protein possessing hph and HSV-I TK enzymatic activities was obtained by inserting translation termination codons into the HyTK (SEQ ID NO:1 selectable fusion gene (in tgLS(+)HyTK/stop; FIG. 2), downstream of the hph-derived sequences, but upstream of the HSV-I TK-derived sequences. As would be expected if the HyTK (SEQ ID NO:1 selectable fusion gene encoded bifunctional fusion protein, insertion of the translation termination codons left the ability of the virus to confer Hm$^r$ intact, but abolished the ability of the retrovirus to transduce HAT$^r$ (Table 3). When compared with the HSV-I TK gene in Rat-2 cells, the HyTK (SEQ ID NO:1 selectable fusion gene was slightly less effective at conferring ability to grow in HAT medium (Table 1), but markedly more effective at conferring GCV$^s$ (FIG. 4). These observations cannot be explained on the basis of the relative steady state levels of mRNA expression (FIG. 5), nor on the basis of changes in the stability of the HyTK (SEQ ID NO:1 selectable fusion protein. The apparent contradiction might be explained by hypothesizing that the HSV-I TK-derived moiety of the HyTK (SEQ ID NO:1 selectable fusion protein possesses a substrate affinity different from that of the wild-type HSV-I TK protein (possibly due to conformational change), with a reduced ability to phosphorylate thymidine and an increased ability to phosphorylate GCV. Altered substrate affinities have been noted previously in a number of pathogenic drug-resistant strains of HSV-I, which encode mutant TK protein that exhibit a reduced ability to phosphorylate thymidine analogs, yet retain the ability to phosphorylate thymidine (Larder et al., *J. Biol. Chem.* 258:2027, 1983; Palu et al., *Virus Res.* 13:303, 1989; Larder and Darby, *Antiviral Res.* 4:1, 1984). The slightly increased efficiency with which the HyTK (SEQ ID NO:1 selectable fusion gene confers Hm$^r$, relative to the hph gene (Table 1), may be due to an increase in protein stability, or an increased specific activity of the phosphotransferase.

Figure 7:
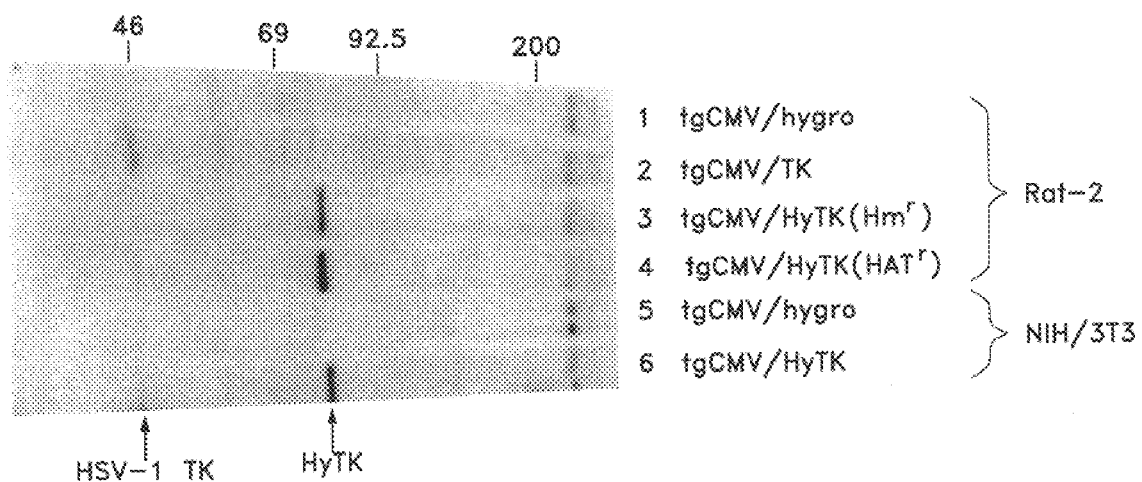
FIG. 7 is a half tone photograph of a gel on which [$^{35}$S]-labelled proteins extracted from NIH/3T3 cells or Rat-2 cells transfected with tgCMV/hygro, tgCMV/TK or tgCMV/HyTK were immunoprecipitated with a rabbit polyclonal antiserum raised against HSV-I TK.

Moreover, as shown in FIG. 7, a single approximately 76 kD protein was specifically immunoprecipitated by a rabbit polyclonal antiserum directed against HSV-I TK from extracts of cells expressing the HyTK (SEQ ID NO:1 selectable fusion gene. Thus, the phenotype conferred by the HyTK (SEQ ID NO:1 selectable fusion gene. was not due to internal translation initiation in the HSV-I TK-derived moiety of the gene, and the HyTK (SEQ ID NO:1 selectable fusion gene does indeed encode a bifunctional selectable fusion gene.

Example 4

Figure 8:
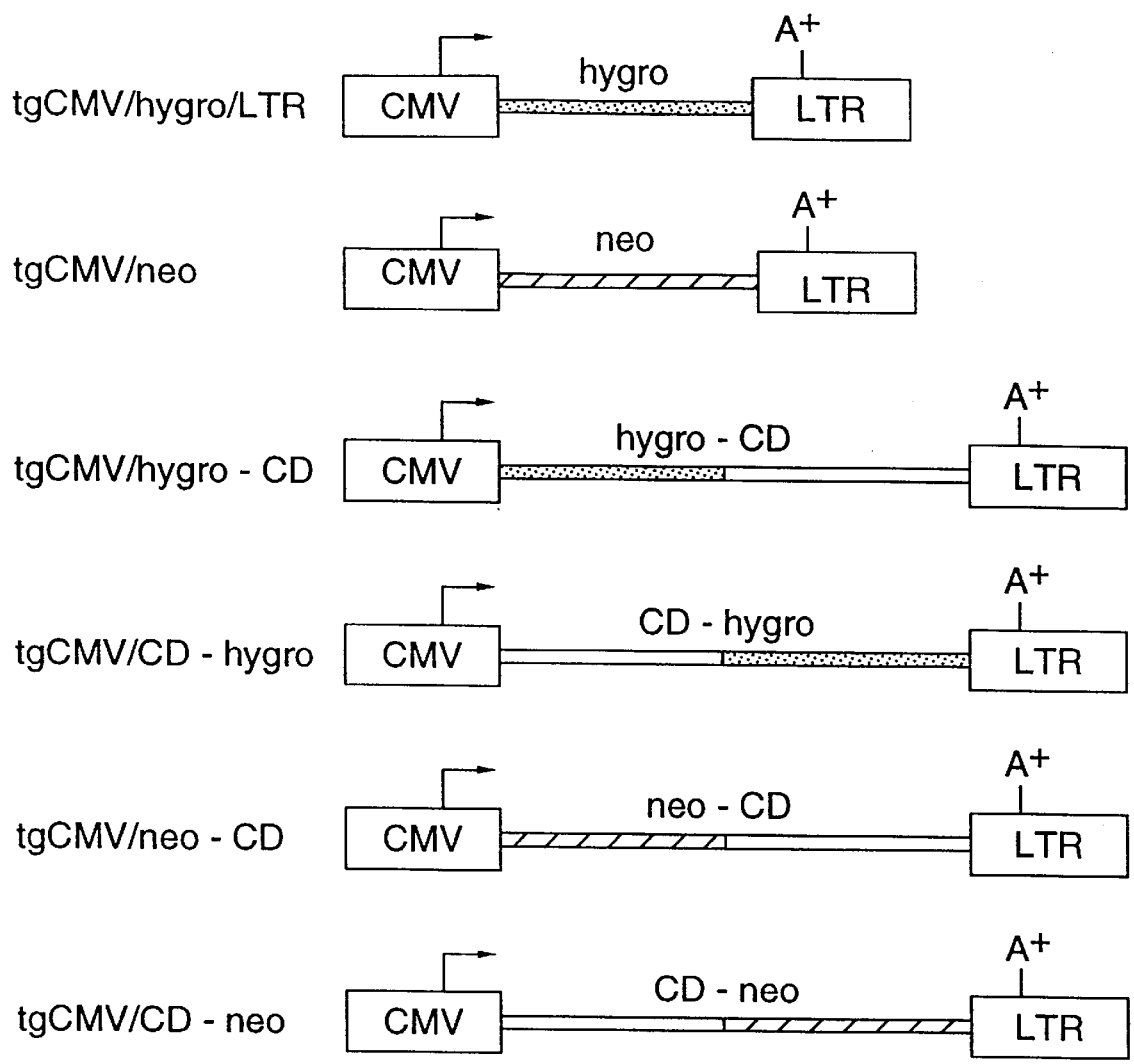
FIG. 8 shows diagrams of the expression cassettes contained in plasmids tgCMV/hygro/LTR, tgCMV/neo, tgCMV/hygro-CD, tgCMV/CD-hygro, tgCMV/neo-CD and tgCMV/CD-neo. The horizontal arrows indicate transcriptional start sites and direction of transcription. The open box labeled LTR is the retroviral long terminal repeat. The open box labeled CMV is the cytomegalovirus promoter.

Construction and Characterization of Plasmid Vectors Containing CD-neo Selectable Fusion Gene A. Construction of the Bifunctional CD-neo Selectable Fusion Gene. Plasmid tgCMV/hygro/LTR (FIG. 8) consists of the following elements: the BalI-SstII fragment containing the HCMV IE94 promoter (Boshart et al., *Cell* 41:521, 1985); an oligonucleotide containing a sequence conforming to a consensus translation initiation sequence for mammalian cells (GCCGCCACC ATG) (SEQ ID NO:5) (Kozak et al., *Nucl. Acids Res.* 15:8125, 1987); nucleotides 234–1256 from the hph gene (Kaster et al., *Nucl. Acids Res.* 11:6895, 1983), encoding hygromycin phosphotransferase; sequences from nucleotide 7764 and through the 3' LTR of MoMLV (Shinnick et al., *Nature* 293:543, 1981), containing a polyadenylation sequence; the NruI-AlwNI fragment from pML2d (Lusky and Botchan, *Nature* 293:79, 1981), containing the bacterial replication origin; the AlwNI-AatII fragment from pGEM1 (Promega Corp.), containing the β-lactamase gene.

Plasmids tgCMV/neo, tgCMV/CD,tgCMV/CD-hygro, tgCMV/neo-CD, and tgCMV/CD-neo are all similar in structure to tgCMV/hygro/LTR and contain the consensus translation initiation sequence; however, each contains different sequences in place of the hph sequences. Plasmid tgCMV/neo contains an oligonucleotide encoding three amino acids (GGA TCG GCC) (SEQ ID NO:7) Nahd nucleotide 154–945 from the bacterial neo gene encoding neomycin phosphotransferase (Beck et al., *Gene* 19:327, 1982), in place of the hph sequences. Plasmid tgCMV/CD contains nucleotides 1645–2925 from the bacterial CD gene encoding cytosine deaminase (Genbank accession number X63656), in place of the hph sequences. The CD sequences were amplified by PCR from plasmid pCD2 (Mullen et al., *Proc. Natl. Acad. Sci. USA* 89:33, 1992). Plasmid tgCMV/hygro-CD contains nucleotides 234–1205 from the hph gene fused to nucleotides 1645–2925 from the CD gene in place of the hph sequences. Plasmid tgCMV/CD-hygro contains nucleotides 1645–2922 from the CD gene fused to nucleotides 234–1256 from the hph gene in place of the hph sequences. Plasmid tgCMV/neo-CD contains an oligonucleotide encoding an additional three amino acids (GGA TCG GCC) (SEQ ID NO:7) and nucleotides 154–942 from the bacterial neo gene fused to nucleotides 1645–2925 from the CD gene in place of the hph sequences. Plasmid tgCMV/CD-neo contains nucleotides 1645–2922 from the CD gene fused to nucleotides 154–945 from the neo gene in place of the hph sequences.

Plasmid tgCVM/hygro/LTR was constructed using standard techniques (Ausubel et al., *Current Protocols in Molecular Biology* (Wiley, New York), 1987) as follows: Plasmid HyTK-CMV-IL2 was constructed first by ligating the large HindIII-StuI fragment from tgLS(+)HyTK (Lupton et al., *Mol. Cell. Biol.* 11:3374, 1991) with the HindIII-StuI fragment spanning the HCMV IE94 promoter from tgLS(−) CMV/HyTK (Lupton et al., supra, 1991), and a fragment containing human IL-2 cDNA sequences. The fragment containing human IL-2 cDNA sequences was amplified from a plasmid containing the human-IL-2 cDNA by PCR using oligonucleotides 5'-CCCGCTAGCCGCCACCATGTAC AGGATGCAACTCC-3'(SEQ ID NO:8) and 5'-CCCGTCGACTTAATTATCAAGTCAGTGTT-3'(SEQ ID NO:9). Following amplification, the PCR product was first treated with T4 DNA polymerase to render the ends blunt, then digested with NheI, before ligation to the fragments from tgLS(+)HyTK and tgLS(−)CMV/HyTK. To generate plasmid tgCVM/hygro/LTR, the SalI-PvuI fragment spanning the SV40 polyadenylation signal of tgCVM/hygro (Lupton et al., supra, 1991) was replaced with the SalI-PvuI fragment containing the Moloney leukemia virus LTR (which contains the retroviral polyadenylation signal) from HyTK-CMV-IL2.

Plasmid tgCMV/neo was constructed using standard techniques (Ausubel et al., supra, 1987) as follows: A PvuI-NheI fragment spanning the HCMV IE94 promoter from tgCVM/hygro was ligated to a NheI-HindIII fragment spanning the neo gene from tgLS(+)neo (the HindIII site was treated with T4 DNA polymerase to render the end blunt) and ligated to SalI-PvuI fragment containing the Moloney leukemia virus LTR (which contains the retroviral polyadenylation signal) from HyTK-CMV-IL2.

Plasmid tgCMV/CD was constructed using standard techniques (Ausubel et al., supra, 1987) as follows: A PvuI-NheI fragment spanning the HCMV IE94 promoter from tgCMV/hygro was ligated to a synthetic DNA fragment (prepared by annealing oligonucleotides 5'-CTAGCCGCCAC CATGTC-GAATAACGCTTTACAAACAATTATTAACG CCCG-3'(SEQ ID NO:10) and 5'-GTAACCGGGCGTTAATAATTGTTTGTAAAGCGT TATTCGACATGGTGGCGG-3'(SEQ ID NO:11), the BstE2-AluI fragment containing the remainder of the CD coding region from pCD2 (Mullen et al., Proc. Natl. Acad. Sci. USA 89:33, 1992), and the SalI-PvuI fragment containing the Moloney leukemia virus LTR (which contains the retroviral polyadenylation signal) from HyTK-CMV-IL2. The SalI site in the latter fragment was treated with T4 DNA polymerase to render the end blunt before ligation.

Plasmid tgCMV/CD-hygro was constructed using standard techniques (Ausubel et al., supra, 1987) as follows: The large ClaI-SalI fragment from tgCMV/CD was ligated to a ClaI-NcoI fragment amplified from tgCMV/hygro by PCR using oligonucleotides 5'-CCCATCGATTACAAACGTAAAAAGCCTGAACTC ACCGCGAC-3'(SEQ ID NO:12) and 5'-GCCATGTAGTGTATTGACCGATTCC-3'(SEQ ID NO:13) (the PCR product was digested with ClaI and NcoI before ligation), and an NcoI-SalI fragment containing the remainder of the hph coding region from tgCMV/hygro/LTR.

Plasmid tgCMV/hygro-CD was constructed using standard techniques (Ausubel et al., supra, 1987) as follows: The large SpeI-BstE2 fragment from tgCMV/CD was ligated to a SpeI-ScaI fragment containing the hph coding region from tgCMV/hygro/LTR, and a synthetic DNA fragment (prepared by annealing oligonucleotides 5'-ACTCTCGAAT AACGCTTTACAAACAATTATTAACGCCCG-3'(SEQ ID NO:14) and 5'-GTAACCGGGCGTTAATAATTGTTTGTAAAGCGTT ATTCGAGAGT-3'(SEQ ID NO:15)).

Plasmid tgCMV/CD-neo was constructed using standard techniques (Ausubel et al., supra, 1987) as follows: The large ClaI-Asp718 fragment from tgCMV/CD was ligated to a synthetic DNA fragment (prepared by annealing oligonucleotides 5'-CGATTACAAACGTATTGAACAA GATGGATTGCACGCAGGTTCTCC-3'(SEQ ID NO:16) and 5'-GGCCGGAGAACCTGCGTGCA ATCCATCTTGTTCAATACGTTTGTAAT-3'(SEQ ID NO:17)) and an EagI-Asp718 fragment containing the remainder of the neo gene coding region from tgCMV/neo.

Plasmid tgCMV/neo-CD was constructed using standard techniques (Ausubel et al., supra, 1987) as follows: The large SphI-SalI fragment from tgCMV/neo was ligated to a ClaI-NcoI fragment amplified from tgCMV/neo by PCR using oligonucleotides 5'-CGAACTGTTCGCCAGGCTC-3'(SEQ ID NO:18) and 5'-CCCGGTAACCGGGCGTTAATAATTGTTTGTAAA GCGTTATTCGAGAA GAACTCGTCAAGAAGGC-31' (SEQ ID NO:19) (the PCR product was digested with SphI and BstE2 before ligation), and a BstE2-SalI fragment containing the remainder of the CD gene coding region from tgCMV/CD.

B. Dominant Positive Selection of Cells containing CD Fusion Genes. To demonstrate that the CD fusion gene encode neo or and hph activities, the frequencies with which the various plasmids conferred drug resistance in NIH/3T3 cells were determined.

First, NIH/3T3 cells were grown in Dulbecco Modified Eagle Medium (DMEM; available from Gibco Laboratories) supplemented with 10% bovine calf serum (Hyclone), 2 mM L-glutamine, 50 U/ml penicillin, and 50 $\mu$g/ml streptomycin at 37° C. in a humidified atmosphere supplemented with 10% $CO_2$. For transfection, exponentially growing cells were harvested by trypsinization, washed free of serum, and resuspended in DMEM at a concentration of $10^7$ cells/ml. Plasmid DNA (5 $\mu$g) was added to 800 $\mu$l of cell suspension ($8\times10^6$ cells), and the mixture was subjected to electroporation using the Biorad Gene Pulser and Capacitance Extender (200–300 V, 960 $\mu$F, 0.4 cm electrode gap, at ambient temperature).

Following electroporation, the cells were returned to 10 cm dishes and grown in non-selective medium. After 24 hours, the cells were trypsinized, seeded at $6\times10^5$ cells/10 cm dish, and allowed to attach overnight. The non-selective medium was replaced with selective medium (containing 500 U/ml of Hm or 800 $\mu$g/ml of G-418), and selection was continued for 10–14 days. The plates were then fixed with methanol, stained with methylene blue and colonies were counted. The number of colonies reported in Table 4 is the average number of colonies per 10 cm dish.

Untransfected cells were not hygromycin resistant ($Hm^r$) or G-418 resistant ($G-418^r$). The results indicate that the hygro-CD and CD-hygro fusion genes encode $Hm^r$, but the activity of the CD-hygro fusion gene is lower than that of the hygro-CD fusion gene. The CD-neo (SEQ ID NO:3 fusion gene confers $G-418^r$, but the neo-CD fusion gene does not.

TABLE 4

| Transfected Plasmid | Dominant Positive Selection | | | |
|---|---|---|---|---|
| | No. $Hm^r$ Colonies | | No. $G-418^r$ Colonies | |
| | Trial 1 | Trial 2 | Trial 1 | Trial 2 |
| None | 0 | 0 | 0 | 0 |
| tgCMV/hygro/LTR | 89 | 34 | nt | nt |
| tgCMV/hygro-CD | 96 | 34 | nt | nt |
| tgCMV/CD-hygro | 7[b] | 13[b] | nt | nt |
| tgCMV/neo | nt | nt | 28 | 73 |
| tgCMV/neo-CD | nt | nt | 0 | 0 |
| tgCMV/CD-neo | nt | nt | 29 | 64 | nt = not tested
b = small, slowly growing colonies

C. Cytosine Deaminase Assay on Transfected Cell Pools. To determine whether the fusion genes had retained cytosine deaminase (CD) activity, the $Hm^r$ and $G-418^r$ NIH/3T3 colonies, as reported in Table 4, were pooled and expanded into cell lines. Extracts were prepared and assayed for CD activity by measuring the conversion of cytosine to uracil essentially as previously described (Mullen et al., *Proc. Natl. Acad. Sci. USA* 89:33, 1992), except that [$^{14}$C]-cytosine was used in placed of [$^3$H]-cytosine. A 10 cm dish was seeded with 1×10$^6$ cells, and the cells were incubated for two days. The cells were then washed in Tris buffer (100 mM Tris, pH 7.8, 1 mM EDTA, 1 mM dithiothreitol) and scraped from the dish in 1 ml of Tris buffer. The cells were then centrifuged for 10 sec at 24,000 rpm in an Eppendorf microfuge, resuspended in 100 µl of Tris buffer and subjected to five cycles of rapid freezing and thawing. Following centrifugation for 5 min at 6,000 rpm in an Eppendorf microfuge, the supernatant was transferred to a clean tube.

Figure 9:
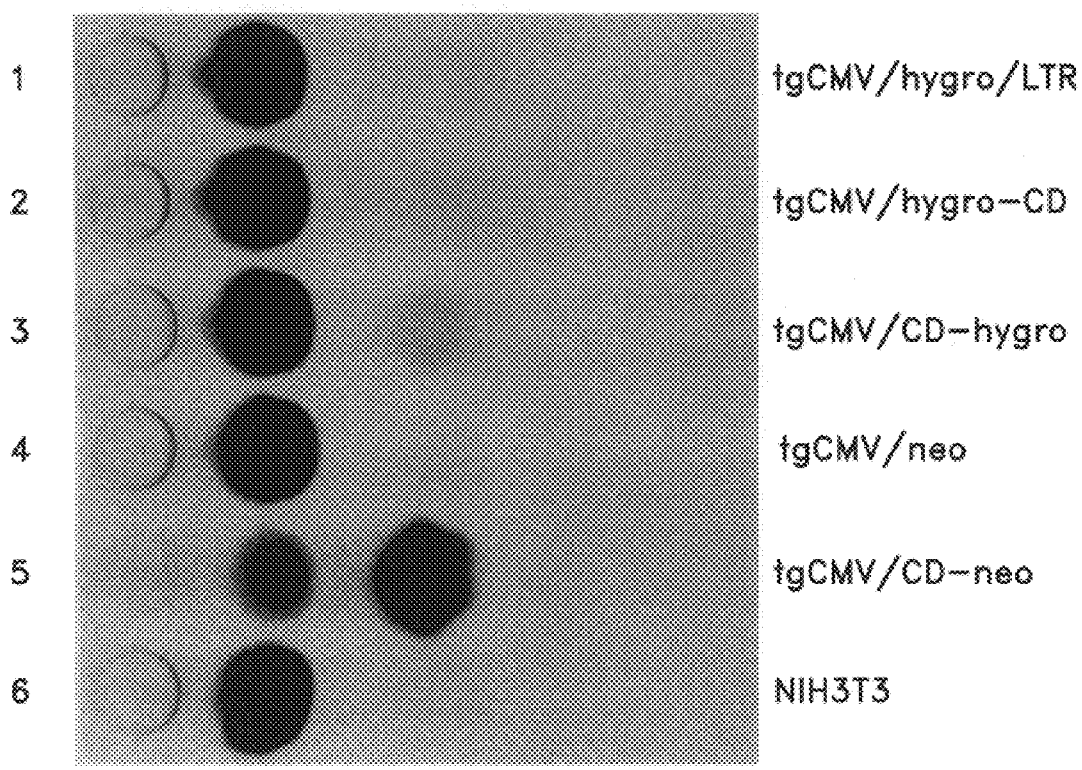
FIG. 9 shows the results of the cytosine deaminase assay on extracts prepared from transfected pools of NIH/3T3 cells. The extracts were assayed by measuring the conversion of cytosine to uracil.

The concentration of protein in the extract was determined using a Biorad protein assay kit. A 25 µl aliquot of cell extract (or an equivalent amount of protein in a volume of 25 µl) was then mixed with 1 µl of [$^{14}$C]-cytosine (0.6 mCi/ml, 53.4 mCi/mmol; Sigma Chemical Co.), and the reaction allowed to proceed at 37° C. for 1–4 h. One half of the reaction was then applied to a thin-layer chromatogram and chromatographed in a mixture of 86% 1-butanol and 14% water. Following development, the thin-layer chromatogram was exposed to Kodak X-OMAT AR X-ray film for 8–14 h. The result is shown in FIG. 9.

The results indicate that the CD-neo (SEQ ID NO:3 CD-hygro and hygro-CD fusion genes encoded CD activity, but the activities of the CD-hygro and hygro-CD fusion genes were lower than that of the CD-neo (SEQ ID NO:3 fusion gene.

Example 5

Construction and Characterization of Retroviral Vectors Containing neo or CD-neo (SEQ ID NO:3 Selectable Fusion Genes A. Construction of Retroviral Vectors. The retroviral plasmids tgLS(+)neo and tgLS(+)CD-neo consist of the following elements: the 5' LTR and sequences through the PstI site at nucleotide 984 of MoMSV (Van Beveren et al., *Cell* 27:97, 1981); sequences from the PstI site at nucleotide 563 to nucleotide 1040 of MoMLV (Shinnick et al., *Nature* 293:543, 1981); a fragment from tgCMV/neo or tgCMV/CD-neo (SEQ ID NO:3 containing the neo or CD-neo coding regions, respectively; sequences from nucleotide 7764 and through the 3' LTR of MoMLV (Shinnick et al., supra, 1981); the NruI-AIwNI fragment from pML2d (Lusky and Botchan, supra, 1981), containing the bacterial replication origin; the AIwNI-AatII fragment from pGEM1 (Promega Corp.), containing the β-lactamase gene.

Plasmid tgLS(+)neo was constructed using standard techniques (Ausubel et al., supra, 1987) as follows: Plasmid tgLS(+)hygro was constructed first, by ligating an EcoRI-ClaI fragment from tgLS(+)HyTK to an EcoRI-Asp718 fragment from tgCMV/hygro, and a synthetic DNA fragment (prepared by annealing oligonucleotides 5'-GTACAAGCTTGGATCCCTCGAGAT-31'(SEQ ID NO:20) and 5'-CGATCTCGAGGGATCCAAGCTT-3') (SEQ ID NO:21). Plasmid tgLS(+)neo was then constructed by replacing the NheI-HindIII fragment spanning the hygro gene with a NheI-HindIII fragment amplified from pSV2neo (Southern and Berg, *J. Mol. Appl. Gen.* 1:327, 1982) by PCR using oligonucleotides 5'-CCCGCTAGCCGCCGCCACCA TGGGATCGGCCATTGAACAAGATGGATTGCAC-31' (SEQ ID NO:22) and 5'-CCCAAGCTTCCCGCTCAGAAGAACTCGTC-3'(SEQ ID NO:23) (the PCR product was digested with NheI and HindIII before ligation).

Plasmid tgLS(+)CD-neo was constructed using standard techniques (Ausubel et al., supra, 1987) as follows: The NheI-SalI fragment spanning the HCMV IE94 promoter and human IL-2 cDNA from HyTK-CMV-IL2 was replaced with the NheI-SalI fragment from tgCMV/CD-neo.

Figure 10:
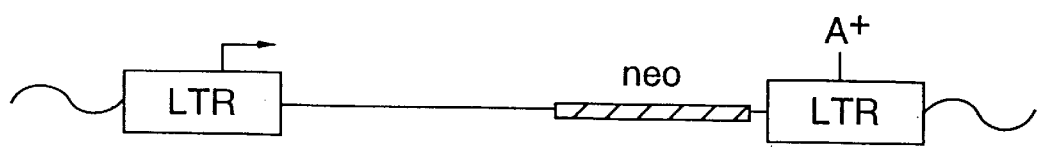
FIG. 10 shows diagrams of the proviral structures of retroviral vectors tgLS(+)neo and tgLS(+)CD-neo used in the present invention.
Figure 10:
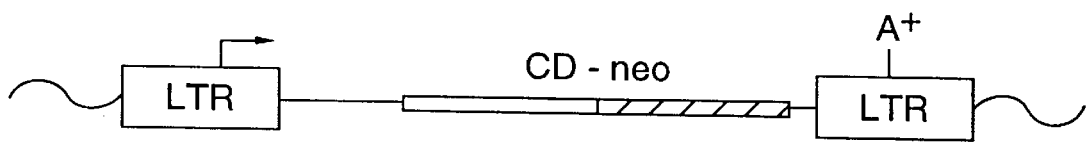

FIG. 10 shows the proviral structures of the retroviral vectors tgLS(+)neo and tgLS(+)CD-neo. In the figure "LTR" signifies the long terminal repeat segments of the retroviral vector, "neo" signifies the bacterial neomycin phosphotransferase gene, and "CD-neo" represents the CD/neomycin phosphotransferase fusion gene. The neo and CD-neo (SEQ ID NO:3 genes are operably linked to the LTR transcriptional control region. The arrows show the direction of transcription from the transcriptional control regions. "A$^+$" represents the polyadenylation sequence.

B. Generation of Stable Cell Lines Infected With Retroviral Vectors. To derive stable NIH/3T3 cell lines infected with tgLS(+)neo and tgLS(+)CD-neo, the retroviral plasmid DNAs were transfected into Ψ2 ecotropic packaging cells. The transfected Ψ2 cells were then transferred to a 10 cm tissue culture dish containing 10 ml of complete growth medium supplemented with 10 mM sodium butyrate (Sigma Chemical Co.) and allowed to attach overnight. After 15 h, the medium was removed and replaced with fresh medium. After a further 24 hours, the medium containing transiently produced ecotropic virus particles was harvested, centrifuged at 2000 rpm for 10 minutes and used to infect NIH/3T3 cells.

Exponentially dividing NIH/3T3 cells were harvested by trypsinization and seeded at a density of 2.5×10$^4$ cells/35 mm well in two 6-well tissue culture trays. On the following day, the medium was replaced with serial dilutions of virus-containing, cell-free supernatant (1 ml/well) in medium supplemented with 4 µg/ml Polybrene hexadimethrine bromide (Sigma Chemical Co.). Infection was allowed to proceed overnight. Then the supernatant was replaced with complete growth medium. After a further 8–24 hours of growth, the infected NIH/3T3 cells were selected for drug resistance to G-418 (Gibco) at a final concentration of 800 µg/ml (Hm$^r$ cells). After a total of 12–14 days of growth, one tray of cultured G-418$^r$ resistant cells was fixed with 100% methanol and stained with methylene blue. The colonies were counted and the number of colonies in each well was used to establish the titers of the retrovirus present in the transiently infected supernatant (Table 5).

TABLE 5

Titers of Ecotropic Retroviruses Produced Transiently in Ψ2 Packaging Cells on NIH/3T3 Cells

| Virus | G-418$^r$ CFU/ml |
|---|---|
| tgLS(+)neo | 5 × 10$^5$ |
| tgLS(+)CDneo | 1 × 10$^5$ |

From the other tray of G-418$^r$ cells, the colonies of G-418$^r$ cells were pooled and expanded into bulk cultures for analysis. Extracts were prepared from the bulk cultures and assayed for CD activity by measuring the conversion of cytosine to uracil generally as previously described (Mullen et al., 1992), except that [$^{14}$C]-cytosine was used in place of [$^3$H]-cytosine. A 10 cm dish was seeded with 1×10$^6$ cells, and the cells were incubated for 2 days. The cells were then washed in Tris buffer (100 mM Tris, pH 7.8, 1 mM EDTA, 1 mM dithiothreitol) and scraped from the dish in 1 ml of Tris buffer.

Figure 11:
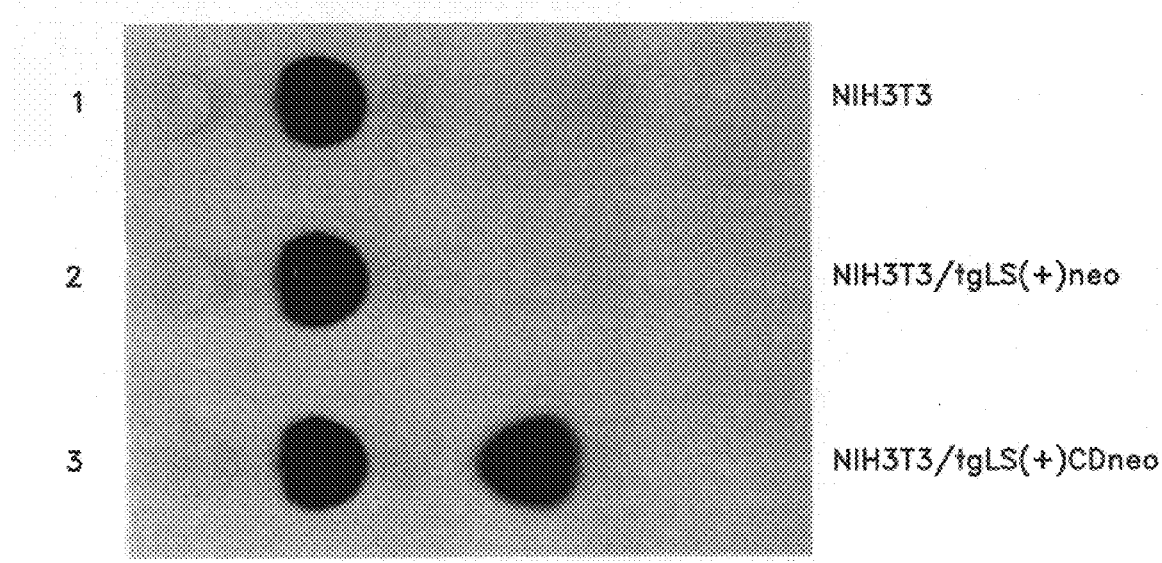
FIG. 11 shows the results of the cytosine deaminase assay on uninfected (lane 1), tgLS(+)neo-infected (lane 2) and tgLS(+)CD-neo-infected NIH/3T3 (lane 3) cell pools. The results indicate that cells infected with the tgLS(+)CD-neo express high levels of cytosine deaminase activity.

The cells were then centrifuged for 10 seconds at 14,000 rpm in an Eppendorf microfuge, resuspended in 100 μl of Tris buffer and subjected to five cycles of rapid freezing and thawing. Following centrifugation for 5 min at 6,000 rpm in an Eppendorf microfuge, the supernatant was transferred to a clean tube. The concentration of protein in the extract was determined using a Biorad protein assay kit. A 25 μl aliquot of cell extract (or an equivalent amount of protein in a volume of 25 μl) was then mixed with 1 ml of [$^{14}$C]-cytosine (0.6 mCi/ml, 53.4 mCi/mmol; Sigma Chemical Co.), and the reaction was allowed to proceed at 37° for 1–4 hours. One half of the reaction mixture was then applied to a thin-layer chromatogram, and chromatographed in a mixture of 86% 1-butanol and 14% water. Following development, the thin-layer chromatogram was exposed to Kodak X-OMAT AR X-ray film for 8–14 hours. The results shown in FIG. 11 indicate that cells infected with the tgLS(+)CD-neo retroviral vector express high levels of cytosine deaminase activity.

C. Negative Selection of Cells Containing the CD-neo (SEQ ID NO:3 Selectable Fusion Gene. To investigate the utility of the neo and CD-neo (SEQ ID NO:3 selectable fusion genes for negative selection, the colonies resulting from each transfection were pooled and expanded into cell lines for further analysis. The NIH/3T3 cells, or NIH/3T3 cells infected with the tgLS(+)neo or tgLS(+)CD-neo retroviruses were assayed for 5-FC$^s$ using a long-term proliferation assay.

First, 1×10$^4$ cells were seeded into 10 cm tissue culture dishes in complete growth medium and allowed to attach for 4 hours. The medium was then supplemented with various concentrations of G-418 and/or 5-FC (Sigma), after which the cells were incubated for a further 10–14 days. The medium was replaced every 2–4 days. The cells were then fixed in situ with 100% methanol and stained with methylene blue.

Figure 12:
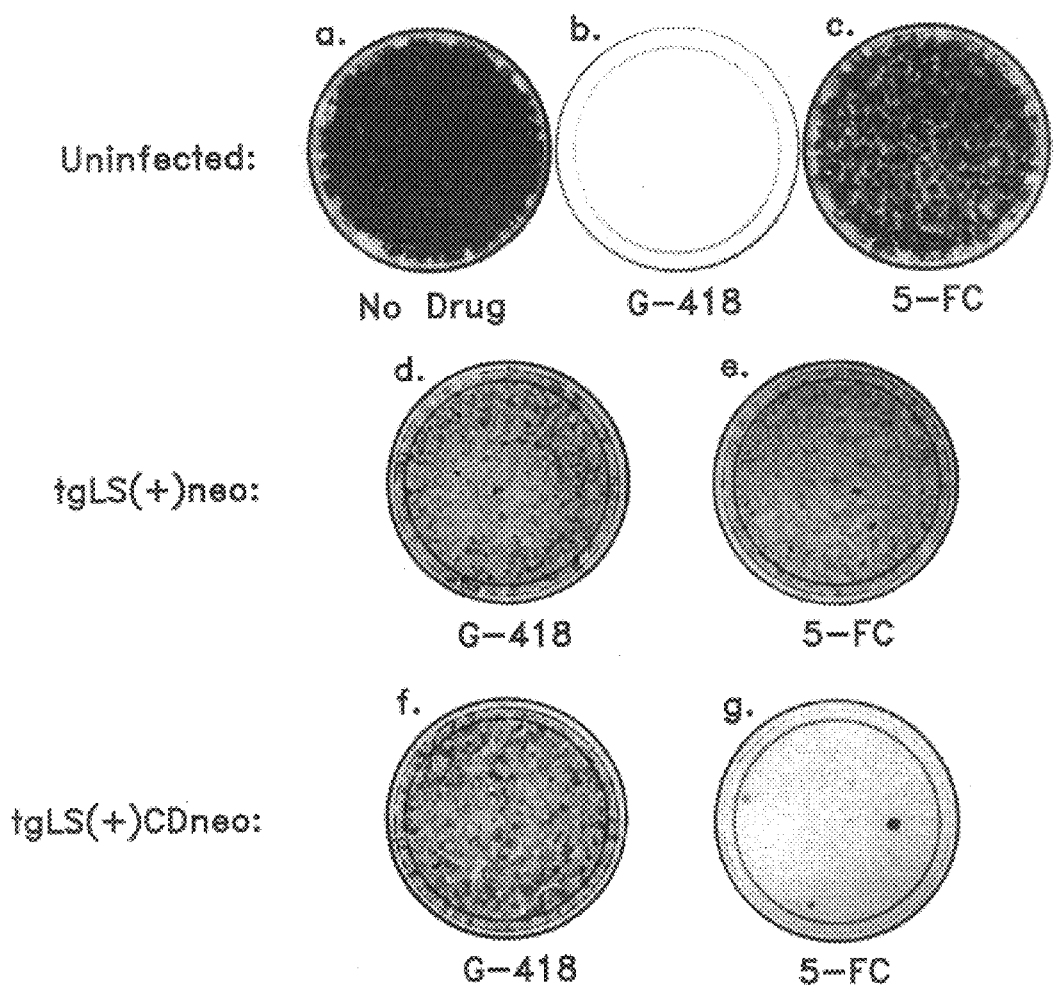

Photographs of representative stained plates are shown in FIG. 12. Plate a had NIH/3T3 cells grown in drug-free medium. Plate b had NIH/3T3 cells grown in medium containing 800 μg/ml G-418. Plate c had NIH/3T3 cells grown in medium containing 100 μg/ml 5-FC. Plate d had NIH/3T3 cells infected with tgLS(+)neo and grown in medium containing 800 μg/ml G-418. Plate e had NIG 3T3 cells infected with tgLS(+)neo and grown in medium containing 800 μg/ml G-418 and 100 μg/ml 5-FC. Plate f had NIH/3T3 cells infected with tgLS(+)CD-neo and grown in medium containing 800 μg/ml G-418. Plate g had NIH/3T3 cells infected with tgLS(+)CD-neo and grown in medium containing 800 μg/ml G-418 and 100 μg/ml 5-FC.

These results indicate that 1) uninfected NIH/3T3 cells are sensitive to G-418 and resistant to 5-FC, 2) NIH/3T3 cells infected with tgLS(+)neo are resistant to both G-418 and 5-FC, and 3) NIH/3T3 cells infected with tgLS(+)CD-neo are resistant to G-418 but sensitive to 5-FC.

I claim:

1. A selectable fusion gene comprising a dominant positive selectable gene fused to and in reading frame with a negative selectable gene, wherein the selectable fusion gene encodes a single bifunctional fusion protein which when expressed confers a dominant positive selectable phenotype and a negative selectable phenotype on a cellular host.

2. A selectable fusion gene according to claim 1, wherein the dominant positive selectable gene is selected from the group consisting of hph, neo, gpt and the negative selectable gene is selected from the group consisting of HSV-I TK, VZV TK, HPRT, APRT and gpt.

3. A selectable fusion gene according to claim 1, wherein the dominant positive selectable gene is hph and the negative selectable gene is HSV-I TK.

4. A selectable fusion gene according to claim 3 encoding the sequence of amino acids 1–691 of SEQ ID NO:2.

5. A selectable fusion gene according to claim 4 comprising the sequence of nucleotides 1–2073 of SEQ ID NO:1.

6. A recombinant expression vector comprising a selectable fusion gene according to claim 1.

7. A recombinant expression vector according to claim 6, wherein the vector is a retrovirus.

8. A cell transduced with a recombinant expression vector according to claim 6.

9. A method for conferring a dominant positive and negative selectable phenotype on a cell, comprising the step of transducing the cell with a recombinant expression vector according to claim 6.

10. A method for isolating cells having a negative selectable phenotype comprising the steps of:

(a) transducing a population of cells with a recombinant expression vector having a dominant positive selectable gene fused to and in reading frame with a negative selectable gene, thereby conferring the cells with a dominant positive selectable phenotype and a negative selectable phenotype;

(b) applying positive selection to select cells having a dominant positive selectable phenotype, thereby concomitantly selecting cells having a negative selectable phenotype.

\* \* \* \* \*